United States Patent
Park et al.

(10) Patent No.: US 11,458,084 B2
(45) Date of Patent: Oct. 4, 2022

(54) HAIR CLEANSING COMPOSITION

(71) Applicant: L'OREAL, Paris (FR)

(72) Inventors: Angela Park, Carlstadt, NJ (US); Pedro Aprigliano, Rio de Janeiro (BR)

(73) Assignee: L'OREAL, Paris (FR)

( * ) Notice: Subject to any disclaimer, the term of this patent is extended or adjusted under 35 U.S.C. 154(b) by 154 days.

(21) Appl. No.: 16/804,948

(22) Filed: Feb. 28, 2020

(65) Prior Publication Data
US 2021/0267867 A1   Sep. 2, 2021

(51) Int. Cl.
| | |
|---|---|
| *A61Q 5/02* | (2006.01) |
| *A61K 8/46* | (2006.01) |
| *A61K 8/41* | (2006.01) |
| *A61K 8/34* | (2006.01) |
| *A61K 8/92* | (2006.01) |
| *A61K 8/58* | (2006.01) |
| *A61K 8/42* | (2006.01) |

(52) U.S. Cl.
CPC .............. *A61K 8/463* (2013.01); *A61K 8/342* (2013.01); *A61K 8/416* (2013.01); *A61K 8/42* (2013.01); *A61K 8/585* (2013.01); *A61K 8/922* (2013.01); *A61Q 5/02* (2013.01); *A61K 2800/596* (2013.01)

(58) Field of Classification Search
None
See application file for complete search history.

(56) References Cited

U.S. PATENT DOCUMENTS

| | | | |
|---|---|---|---|
| 5,573,709 A * | 11/1996 | Wells | A61K 8/463 510/122 |
| 9,724,283 B2 * | 8/2017 | Rizk | A61Q 5/02 |
| 2002/0034483 A1 | 3/2002 | Avery et al. | |
| 2002/0192180 A1 | 12/2002 | Fairley et al. | |
| 2003/0024556 A1 | 2/2003 | Guiramand et al. | |
| 2008/0286220 A1 | 11/2008 | Skinner et al. | |
| 2010/0233114 A1 | 9/2010 | Degeorge et al. | |
| 2013/0129648 A1 | 5/2013 | Nguyen et al. | |
| 2013/0284198 A1 | 10/2013 | Mecca et al. | |
| 2014/0335038 A1 | 11/2014 | Bhogal et al. | |
| 2016/0228343 A1 | 8/2016 | Koshti et al. | |
| 2017/0095410 A1 | 4/2017 | Hara et al. | |
| 2018/0271759 A1 | 9/2018 | Brice et al. | |
| 2018/0353410 A1 * | 12/2018 | Kita-Tokarczyk | C07C 219/06 |
| 2019/0029949 A1 | 1/2019 | Ceballos et al. | |
| 2019/0125650 A1 | 5/2019 | Lee et al. | |
| 2019/0365623 A1 | 5/2019 | Botto et al. | |
| 2019/0365619 A1 | 12/2019 | Ceballos et al. | |

\* cited by examiner

*Primary Examiner* — Jyothsna A Venkat
(74) *Attorney, Agent, or Firm* — Polsinelli PC

(57) ABSTRACT

Hair cleansing compositions and methods of use thereof. The hair cleansing composition comprising: (a) about 10 to about 20 wt. % of an sulfate based anionic surfactant; (b) about 1 to about 4 wt. % of amphoteric surfactant; (c) about 4 to about 10 wt. % of a plurality of nonionic surfactants, the plurality of nonionic surfactants comprising: (i) about 1 to about 1.5 wt. % of fatty alcohols, (ii) about 1.5 to about 3 wt. % of glucamide, and (iii) about 1.5 to about 5.5 wt. % of alkanolamide, (d) about 0.5 to 2.5 wt. % of an oil, wherein the oil is a non-silicone oil; and (e) water, wherein all weight percentages are based on the total weight of the hair cleansing composition.

10 Claims, No Drawings

HAIR CLEANSING COMPOSITION

FIELD OF THE DISCLOSURE

The instant disclosure relates to hair cleansing compositions and methods of use thereof. For example, the hair cleansing compositions may be a shampoo.

BACKGROUND OF THE DISCLOSURE

Most "dirt" contains traces of oil and grease, which stick to the surface of the skin and hair. Rinsing with only water is not sufficient to adequately remove the oil and grease. The main functional ingredients in cleansing compositions are surfactants. Surfactants interact with water, thereby allowing it to "wet" surfaces more efficiently. The surfactant-water combination is then able to surround the specks of dirt and carry them away with rinsing. Agitation of the water solution, for example by rubbing hands together during washing or lathering shampoo into hair, also aids the process of removing dirt.

Conventional cleansing compositions such as shampoos, for example, contain surfactants in various amounts. Anionic surfactants are typically included because they provide foaming to a composition. Nonionic surfactants may also be included to provide cleansing and are usually less irritating than anionic surfactants. Nonionic surfactants, however, often exhibit less foaming ability and do not provide any enhancement to viscosity (e.g., often times the composition is thinner and runnier with increased amounts of nonionic surfactants). In some cleansing applications, higher viscosity is desired for the product's handling or ease of application. In addition, higher viscosity personal care products are more aesthetically appealing to many consumers.

The development of cleansing compositions has been driven by a need for certain performance properties that consumers find desirable. For example, consumers seek cleansing compositions that foam and cleanse well, have a certain "thickness" (viscosity), and are mild to the skin and hair. The cleansing compositions should also rinse away from the body with ease. Often, the addition of a particular component to a cleansing composition will enhance one desired property to the detriment of another desired property. It is therefore difficult to achieve a perfect balance of desirable performance properties.

SUMMARY OF THE DISCLOSURE

Aspects of the disclosure relate to hair cleansing compositions and, particularly, hair cleansing compositions having improved foaming characteristics and high levels of an oil. Traditionally, it is recognized that it is difficult to produce hair cleansing compositions, such as shampoos, having non-minimal levels of oil while simultaneously maintaining the level of foam produced by such composition.

The inventors discovered that hair cleansing compositions comprising a unique combination of non-ionic surfactants in certain amounts and ratios in combination with anionic and amphoteric surfactants enable the hair cleansing composition to simultaneously maintain or improve the level of foaming attribute while incorporating non-minimal or high levels of oil. For example, the hair cleansing compositions typically include a total amount of nonionic surfactants of 4 wt. % or more comprising the unique combination of about 1 to about 1.5 wt. % of fatty alcohols, about 1.5 to about 3 wt. % of glucamide, and about 1.5 to about 5.5 wt. % of alkanolamide. Additionally, the foaming characteristics may be improved by formulating the hair cleansing composition to have a weight ratio of the amount of fatty alcohols of (i) to the amount of glucamide of (ii) is 1:1.3 to 1:2.5.

The hair cleansing compositions typically include:
(a) about 8 to about 20 wt. % of a sulfate based anionic surfactant;
(b) about 1 to about 4 wt. % of an amphoteric surfactant;
(c) about 4 to about 10 wt. % of a plurality of nonionic surfactants, the plurality of nonionic surfactants comprising:
  (i) about 1 to about 1.5 wt. % of a fatty alcohol,
  (ii) about 1.5 to about 3 wt. % of a glucamide, and
  (iii) about 1.5 to about 5.5 wt. % of an alkanolamide that is not the glucamide,
(d) about 0.5 wt. % or more of a non-silicone oil; and
(e) water,
  wherein all weight percentages are based on the total weight of the hair cleansing composition.

In some instances, a weight ratio of the amount of fatty alcohols of (i) to the amount of glucamide of (ii) is 1:1.3 to 1:2.5 or, preferably, 1:1.5 to 1:2. The sulfate based anionic surfactant may be selected from sodium lauryl ether sulfate, sodium lauryl sulfate, ammonium lauryl ether sulfate, ammonium lauryl sulfate, and a mixture thereof.

Non-limiting examples of the amphoteric surfactant include those selected from lauryl betaine, lauroamphoglycinate, lauroamphopropylsulfonate, lauroamphopropionate, lauroampho-carboxyglycinate, lauryl sultane, myristamidopropyl betaine, myristyl betaine, myristoamphoglycinate, myristyl propionate, stearoamphoglycinate, stearoamphopropionate, stearoamphopropylsulfonate, stearyl betaine, cocamidoethyl betaine, cocamidopropyl betaine, cocamidopropyl hydroxysultaine, cocamidopropyl dimethylamine propionate, cocoamphoglycinate, cocoamphocarboxypropionate, cocoamphocarboxyglycinate, coco-betaine, cocoamphopropionate, cocoamphopropylsulfonate, and a mixture thereof. Preferably, the amphoteric surfactant is selected from cocamidoethyl betaine, cocamidopropyl betaine, cocamidopropyl hydroxysultaine, cocamidopropyl dimethylamine propionate, cocoamphoglycinate, cocoamphocarboxypropionate, cocoamphocarboxyglycinate, coco-betaine, cocoamphopropionate, cocoamphopropylsulfonate, and a mixture thereof.

The hair cleansing composition may also include a fatty alcohol selected from cetearyl alcohol, cetyl alcohol, stearyl alcohol, behenyl alcohol, arachidyl alcohol, eicosyl alcohol, myristyl alcohol, 2-dodecylhexadecanol, 2-tetradecyl-1-octadecanol, 2-tetradecyl-1-eicosanol, 2-hexadecyl-1-octadecanol, 2-hexadecyl-1-eicosanol, and a mixture thereof. For example, the fatty alcohol may be selected from cetearyl alcohol, cetyl alcohol, stearyl alcohol, and a mixture thereof.

The glucamide of the hair cleansing composition may be selected from acyl glucamides having a carbon chain length of 8 to 20. Suitable glucamides may include those selected from lauroyl/myristoyl methyl glucamide, capryloyl/capryl methyl glucamide, lauroyl methyl glucamide, myristoyl methyl glucamide, capryloyl methyl glucamide, capryl methyl glucamide, cocoyl methyl glucamide, capryloyl/caproyl methyl glucamide, cocoyl methyl glucamide, lauryl methylglucamide, oleoyl methylglucamide oleate, stearoyl methylglucamide stearate, sunfloweroyl methylglucamide, tocopheryl succinate methylglucamide, and a mixture thereof.

The alkanolamides employed in the hair cleansing composition may have a carbon chain containing 2 to 36 carbons. Preferably, the alkanolamides comprise at least one of a fatty acid diethanolamide (DEA), fatty acid monoethanolamides (MEA), fatty acid monoisopropanolamides (MIPA), fatty acid diisopropanolamides (DIPA), or fatty acid glucamides (acyl glucamides). For instance, the alkanolamide may be selected from cocamide MEA, cocamide DEA, soyamide DEA, lauramide DEA, oleamide MIPA, stearamide MEA, myristamide DEA, stearamide DEA, oleylamide DEA, tallowamide DEA lauramide MIPA, tallowamide MEA, isostearamide DEA, isostearamide MEA, and a mixture thereof. Additionally or alternatively, the alkanolamide may be selected from oleic acid diethanolamide, myristic acid monoethanolamide, soya fatty acids diethanolamide, stearic acid ethanolamide, oleic acid monoisopropanolamide, linoleic acid diethanolamide, stearic acid monoethanolamide (Stearamide MEA), behenic acid monoethanolamide, isostearic acid monoisopropanolamide (isostearamide MIPA), erucic acid diethanolamide, ricinoleic acid monoethanolamide, coconut fatty acid monoisopropanolamide (cocoamide MIPA), coconut acid monoethanolamide (Cocamide MEA), palm kernel fatty acid diethanolamide, coconut fatty acid diethanolamide, lauric diethanolamide, polyoxyethylene coconut fatty acid monoethanolamide, coconut fatty acid monoethanolamide, lauric monoethanolamide, lauric acid monoisopropanolamide (lauramide MIPA), myristic acid monoisopropanolamide (Myristamide MIPA), coconut fatty acid diisopropanolamide (cocamide DIPA), and a mixture thereof.

The oil may be a plant based oil, e.g., selected from coconut oil, soybean oil, canola oil, rapeseed oil, corn oil, cottonseed oil, olive oil, palm oil, peanut oil, safflower oil, sesame oil, sunflower oil, linseed oil, palm kernel oil, tung oil, jatropha oil, mustard oil, camelina oil, pennycress oil, castor oil, wheatgerm oil, apricot kernel oil, pistachio oil, poppy oil, pine oil, avocado oil, hazel nut oil, grapeseed oil, colza oil, cade oil, peach kernel oil, coffee bean oil, jojoba oil, and a mixture thereof. In some instances, the plant based oil includes at least coconut oil.

The hair cleansing composition may include about 0.01 to about 10 wt. % of a cationic polymer. For example, the hair cleansing composition may include a cationic polymer selected from polyquaternium 4, polyquaternium 6, polyquaternium 7, polyquaternium 10, polyquaternium 11, polyquaternium 16, polyquaternium 22, polyquaternium 28, polyquaternium 32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, guar hydroxypropyltrimonium chloride, and a mixture thereof.

Additionally or alternatively, the hair cleansing composition may include about 0.1 to about 15 wt. % of a silicone. In some instances, the silicone may be an amino silicone. Non-limiting examples of silicones include amodimethicone, aminoethylaminopropyl dimethicone, aminopropyl dimethicone, and a mixture thereof.

Additional aspects of the disclosure relate to methods of preparing and using such hair cleansing compositions. A method for cleaning hair typically includes:

(a) applying the hair cleansing composition to hair; and
(b) rinsing the hair for removing the hair cleansing composition.

A typical method for preparing the hair cleansing compositions include:
(I) preparing a mixture comprising:
  (a) about 8 to about 20 wt. % of a sulfate based anionic surfactant,
  (b) about 1 to about 4 wt. % of an amphoteric surfactant,
  (c) about 4 to about 10 wt. % of a plurality of nonionic surfactants, the plurality of nonionic surfactants comprising:
    (i) about 1 to about 1.5 wt. % of a fatty alcohol,
    (ii) about 1.5 to about 3 wt. % of a glucamide, and
    (iii) about 1.5 to about 5.5 wt. % of an alkanolamide that is not the glucamide,
  (e) water,
(II) applying heat to the mixture; and
(III) adding (d) about 0.5 wt. % or more of a non-silicone oil before or after applying heat to the mixture,
wherein all weight percentages are based on the total weight of the prepared hair cleansing composition.

DETAILED DESCRIPTION OF THE DISCLOSURE

Additional aspects of the disclosure relate to methods of preparing and using such hair cleansing compositions. Aspects of the disclosure relate to relates to hair cleansing compositions and, particularly, hair cleansing compositions have improved foaming characteristics and high levels of oil, preferably a plant based oil.

Aspects of the disclosure relate to hair cleansing compositions and, particularly, hair cleansing compositions having improved foaming characteristics and non-minimal or high levels of oil, preferably a plant based oil. The hair cleansing compositions typically include:
(a) about 8 to about 20 wt. % of a sulfate based anionic surfactant;
(b) about 1 to about 4 wt. % of an amphoteric surfactant;
(c) about 4 to about 10 wt. % of a plurality of nonionic surfactants, the plurality of nonionic surfactants comprising:
  (i) about 1 to about 1.5 wt. % of a fatty alcohol,
  (ii) about 1.5 to about 3 wt. % of a glucamide, and
  (iii) about 1.5 to about 5.5 wt. % of an alkanolamide that is not the glucamide,
(d) about 0.5 wt. % or more of a non-silicone oil; and
(e) water,
  wherein all weight percentages are based on the total weight of the hair cleansing composition.

The hair cleansing compositions include a unique combination of non-ionic surfactants in an amount of 4 wt. % or more. The unique combination of non-ionic surfactants comprises about 1 to about 1.5 wt. % of fatty alcohols, about 1.5 to about 3 wt. % of glucamide, and about 1.5 to about 5.5 wt. % of alkanolamide. The hair cleansing composition may have a weight ratio of the amount of fatty alcohols to the amount of glucamide of 1:1.3 to 1:2.5. In some instances, the weight ratio of the fatty alcohols to the amount of glucamide is 1:1.5 to 1:2, 1:1.6 to 1:2, 1:1.7 to 1:2, 1:1.5 to 1:1.9, 1:1.5 to 1:1.8, or 1:1.5 to 1:1.17.

The hair cleansing compositions are particularly useful for cleansing and conditioning hair. The hair cleansing compositions exhibit good cleansing ability, lather, foaming and foam stability, and conditioning properties. Additionally, the hair cleansing compositions provide a variety of desirable benefits to the hair, for example, smoothness, detangling, and shine. Accordingly, the hair cleansing compositions may be used in methods for cleansing hair, methods of conditioning hair, and/or methods for imparting smoothness, detangling, and/or shine to hair.

Although the hair cleansing compositions may include silicones, in some instances the hair cleansing composition is free or substantially free of silicone. For example, the hair cleansing composition may have an amount of silicone that is less than 6 wt. %, preferably less than 5 wt. %, preferably less than 4 wt. %, preferably less than 3 wt. %, preferably less than 2 wt. %, preferably less than 1 wt. %, preferably less than 0.5 wt. %, and/or preferably less than 0.1 wt. %, based on the total weight of the hair cleansing composition.

Suitable components, such as those listed below, may be included or excluded from the formulations for the skin-tightening compositions depending on the specific combination of other components, the form of the skin-tightening compositions, and/or the use of the formulation.

Sulfate-Based Anionic Surfactant(s)

The hair cleansing composition includes sulfate-based anionic surfactant typically in the amount of about 8 to about 20 wt. %. For example, the amount of anionic surfactant present in the hair cleansing composition may be about 8 to about 20 wt. %, about 8 to about 18 wt. %, about 8 to about 16 wt. %, about 8 to about 14 wt. %, about 10 to about 20 wt. %, about 10 to about 18 wt. %, about 10 to about 16 wt. %, about 10 to about 14 wt. %, about 12 to about 20 wt. %, about 12 to about 18 wt. %, about 12 to about 16 wt. %, about 12 to about 14 wt. %, including all ranges and subranges therebetween, based on the total weight of the hair cleansing composition.

The term "anionic surfactant" means a surfactant comprising, as ionic or ionizable groups, only anionic groups. These anionic groups are chosen preferably from the groups $CO_2H$, $CO_2$, $SO_3H$, $SO_3$, $OSO_3H$, $OSO_3O_2PO_2H$, $O_2PO_2H$ and $O_2PO_2^{2-}$.

The anionic surfactant(s) may be a sulfate based anionic surfactant such as those selected from alkyl sulfates, alkyl ether sulfates, alkylamido ether sulfates, alkylaryl polyether sulfates, monoglyceride sulfates, or mixtures thereof. Non-limiting examples of other anionic surfactants include alkylsulfonates, alkylamide sulfonates, alkylarylsulfonates, alpha-olefin sulfonates, paraffin sulfonates, alkylsulfosuccinates, alkyl ether sulfosuccinates, alkylamide sulfosuccinates, alkyl sulfoacetates, acylsarcosinates, acylglutamates, alkylsulfosuccinamates, acylisethionates and N-acyltaurates, salts of alkyl monoesters and polyglycoside-polycarboxylic acids, acyllactylates, salts of D-galactoside uronic acids, salts of alkyl ether carboxylic acids, salts of alkyl aryl ether carboxylic acids, and salts of alkylamido ether carboxylic acids; or the non-salified forms of all of these compounds, the alkyl and acyl groups of all of these compounds containing from 6 to 24 carbon atoms and the aryl group denoting a phenyl group. Some of these compounds may be oxyethylenated and then preferably comprise from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfo succinates.

When the anionic surfactant(s) are in salt form, they may be chosen especially from alkali metal salts such as the sodium or potassium salt and preferably the sodium salt, ammonium salts, amine salts and in particular amino alcohol salts, or alkaline-earth metal salts such as the magnesium salt.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts. Alkali metal or alkaline-earth metal salts and in particular the sodium or magnesium salts may be used.

Use is also made of ($C_6$-$C_{24}$)alkyl sulfates, ($C_6$-$C_{24}$)alkyl ether sulfates, which are optionally ethoxylated, comprising from 2 to 50 ethylene oxide units, and mixtures thereof, in particular in the form of alkali metal salts or alkaline-earth metal salts, ammonium salts or amino alcohol salts. More preferentially, the anionic surfactant(s) are chosen from ($C_{10}$-$C_{20}$)alkyl ether sulfates, and in particular sodium lauryl ether sulfate containing 2.2 mol of ethylene oxide.

In some instances, the sulfate based anionic surfactant is selected from sodium lauryl ether sulfate, sodium lauryl sulfate, ammonium lauryl ether sulfate, ammonium lauryl sulfate, and a mixture thereof.

In some instances, the composition of the present disclosure may further comprise a non-sulfate based anionic surfactant such as alkylsulfonates, alkylamide sulfonates, alkylarylsulfonates, alpha-olefin sulfonates, paraffin sulfonates, alkylsulfosuccinates, alkyl ether sulfosuccinates, alkylamide sulfosuccinates, alkyl sulfoacetates, acylsarcosinates, acylglutamates, alkylsulfosuccinamates, acylisethionates and N-acyltaurates, salts of alkyl monoesters and polyglycoside-polycarboxylic acids, acyllactylates, salts of D-galactoside uronic acids, salts of alkyl ether carboxylic acids, salts of alkyl aryl ether carboxylic acids, and salts of alkylamido ether carboxylic acids; or the non-salified forms of all of these compounds, the alkyl and acyl groups of all of these compounds containing from 6 to 24 carbon atoms and the aryl group denoting a phenyl group. Some of these compounds may be oxyethylenated and then preferably comprise from 1 to 50 ethylene oxide units.

Amphoteric Surfactant(s)

The hair cleansing composition includes amphoteric surfactant typically in the amount of about 1 to about 4 wt. %. For example, the amount of amphoteric surfactant present in the hair cleansing composition may be about 1 to about 4 wt. %, about 1 to about 3.5 wt. %, about 1 to about 3 wt. %, about 1 to about 2.5 wt. %, or about 1 to about 2 wt. %; about 1.25 to about 4 wt. %, about 1.25 to about 3.5 wt. %, about 1.25 to about 3 wt. %, about 1.25 to about 2.5 wt. %, or about 1.25 to about 2 wt. %; about 1.5 to about 4 wt. %, about 1.5 to about 3.5 wt. %, about 1.5 to about 3 wt. %, about 1.5 to about 2.5 wt. %, or about 1.5 to about 2 wt. %, including all ranges and subranges therebetween, based on the total weight of the hair cleansing composition.

Suitable examples of the amphoteric surfactant include those selected from lauryl betaine, lauroamphoglycinate, lauroamphopropylsulfonate, lauroamphopropionate, lauro-ampho-carboxyglycinate, lauryl sultane, myristamidopropyl betaine, myristyl betaine, myristoamphoglycinate, myristyl propionate, stearoamphoglycinate, stearoamphopropionate, stearoamphopropylsulfonate, stearyl betaine, cocamidoethyl betaine, cocamidopropyl betaine, cocamidopropyl hydroxysultaine, cocamidopropyl dimethylamine propionate, cocoamphoglycinate, cocoamphocarboxypropionate, cocoamphocarboxyglycinate, coco-betaine, cocoamphopropionate, cocoamphopropylsulfonate, and a mixture thereof. Preferably, the amphoteric surfactant is selected from cocamidoethyl betaine, cocamidopropyl betaine, cocamidopropyl hydroxysultaine, cocamidopropyl dimethylamine propionate, cocoamphoglycinate, cocoamphocarboxypropionate, cocoamphocarboxyglycinate, coco-betaine, cocoamphopropionate, cocoamphopropylsulfonate, and a mixture thereof.

Examples of amphoteric surfactants include betaines, alkyl sultaines, alkyl amphoacetates, alkyl amphoproprionates, and mixtures thereof. Non-limiting examples of amphoteric surfactants are provided below.

Betaines

Useful betaines include those of the following formulae (XIIIa-XIIId):

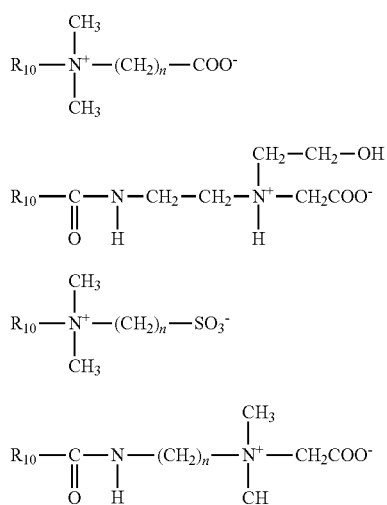

wherein $R_{10}$ is an alkyl group having 8-18 carbon atoms; and n is an integer from 1 to 3.

Examples of betaines that may be suitable in the hair cleansing composition include, for example, coca betaine, cocamidopropyl betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, stearyl betaine, and mixtures thereof. In some cases, the betaine compound is selected from coco betaine, cocamidopropyl betaine, behenyl betaine, capryl/capramidopropyl betaine, and lauryl betaine, and mixtures thereof. Preferably, the betaines include coco betaine and cocamidopropyl betaine.

Alkyl Sulltaines

Non-limiting examples of alkyl sultaines include hydroxyl sultaines of formula (XIV)

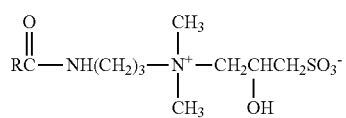

wherein R is an alkyl group having 8-18 carbon atoms. More specific examples include, but are not limited to cocamidopropyl hydroxysultaine, lauryl hydroxysultaine, and a mixture thereof.

Alkyl Amphoacetates and Alkyl Amphodiacetates

Non-limiting examples of alkyl amphoacetates and alkyl amphodiacetates include those of Formula (XV) and (XVI):

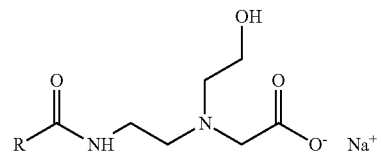

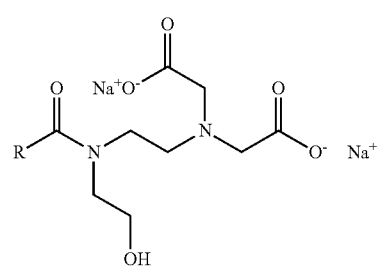

wherein R is an alkyl group having 8-18 carbon atoms. Sodium is shown as the cation in the above formulae above but the cation may be an alkali metal ion such as sodium or potassium, ammonium ions, or alkanolammonium ions such as monoethanolammonium or triethanolammonium ions. A more specific, but non-limiting example, is sodium lauroamphoacetate.

Alkyl Amphopropionates

Non-limiting examples of alkyl amphopropionates include cocoamphopropionate, cornamphopropionatecaprylamphopropionate, cornamphopropionate, caproamphopropionate, oleoamphopropionate, isostearoamphopropionate, stearoamphopropionate, lauroamphopropionate, salts thereof, and a mixture thereof.

Nonionic Surfactant(s)

The hair cleansing compositions include a plurality of nonionic surfactants in an amount that may vary, but typically is in the range of about 4 to about 10 wt. %, based on the total weight of the hair cleansing composition. In some instances, the total amount of the plurality of nonionic surfactants may range from about 4 to about 9 wt. %, about 4 to about 8 wt. %, about 4 to about 7 wt. %, about 4 to about 6.5 wt. %, about 4 to about 6 wt. %, about 4 to about 5.5 wt. %, or about 4 to about 5 wt. %; about 4.5 to about 10 wt. %, about 4.5 to about 9 wt. %, about 4.5 to about 8 wt. %, about 4.5 to about 7 wt. %, about 4.5 to about 6.5 wt. %, about 4.5 to about 6 wt. %, or about 4.5 to about 5.5 wt. %; about 5 to about 10 wt. %, about 5 to about 9 wt. %, about 5 to about 8 wt. %, about 5 to about 7 wt. %, about 5 to about 6.5 wt. %, or about 5 to about 6 wt. %; about 5.5 to about 10 wt. %, about 5.5 to about 9 wt. %, about 5.5 to about 8 wt. %, about 5.5 to about 7 wt. %, or about 5.5 to about 6.5 wt. %, including ranges and sub-ranges therebetween, based on the total weight of the hair cleansing composition The plurality of nonionic surfactants comprises: (i) about 1 to about 1.5 wt. % of fatty alcohols, (ii) about 1.5 to about 3 wt. % of glucamide, and (iii) about 1.5 to about 5.5 wt. % of alkanolamide. The plurality of nonionic surfactants may optionally include other nonionic surfactants in addition to the foregoing nonionic surfactants. As discussed above, the ratio of the nonionic surfactants, particularly the fatty alcohols to glucamide, can be important for maintaining or attaining an improved level of foaming while incorporating non-minimal or high levels of oil (e.g., non-silicone oils and/or plant based oils, such as coconut oil). The hair cleansing composition may have a weight ratio of the amount of fatty alcohols to the amount of glucamide of 1:1.3 to 1:2.5. In some instances, the weight ratio of the fatty alcohols to the amount of glucamide is 1:1.5 to 1:2, 1:1.6 to 1:2, 1:1.7 to 1:2, 1:1.5 to 1:1.9, 1:1.5 to 1:1.8, or 1:1.5 to 1:1.17.

The plurality of nonionic surfactants are further described below.

Fatty Alcohol(s)

The hair cleansing composition includes one or more fatty alcohol, typically, in an amount of about 1 to about 1.5 wt. %, based on the total weight of the hair cleansing composition. In some instances, the amount of fatty alcohol(s) in the hair cleansing composition is about 1 to about 1.4 wt. %, about 1 to about 1.3 wt. %, or about 1 to about 1.2 wt. %; about 1.1 to about 1.5 wt. %, about 1.1 to about 1.4 wt. %, about 1.1 to about 1.3 wt. %, or about 1.1 to about 1.2 wt. %, including ranges and sub-ranges therebetween, based on the total weight of the hair cleansing composition.

Suitable fatty alcohols include those having a fatty group with a carbon chain of greater than 8 carbon atoms, such as 8 to 50 carbon atoms, 8 to 40 carbon atoms, 8 to 30 carbon atoms, 8 to 22 carbon atoms, 12 to 22 carbon atoms, or 12 to 18 carbon atoms, including all ranges and subranges therebetween. In some instances, the fatty group of the fatty alcohols has a carbon chain of 10 to 20 carbon atoms or 10 to 18 carbon atoms. The fatty alcohols may be chosen from polyethylene glycol ethers, such as those having a fatty alcohol group with a carbon chain of 12 to 16 or 12 to 14 carbon atoms.

The fatty alcohol portion is preferably hydrogenated (for example, stearyl, lauryl, cetyl, cetearyl); however, the fatty alcohol may contain one or more double bonds (for example, oleyl). Non-limiting examples of fatty alcohols include decyl alcohol, undecyl alcohol, dodecyl alcohol, myristyl alcohol, lauryl alcohol, cetyl alcohol, stearyl alcohol, cetearyl alcohol (cetyl alcohol and stearyl alcohol), isostearyl alcohol, isocetyl alcohol, behenyl alcohol, linalool, oleyl alcohol, cis-4-t-butylcyclohexanol, isotridecyl alcohol, myricyl alcohol, and a mixture thereof. In some cases, the fatty alcohols comprise at least one of or may be chosen from myristyl alcohol, lauryl alcohol, cetyl alcohol, stearyl alcohol, cetearyl alcohol, isostearyl alcohol, oleyl alcohol, isotridecyl alcohol, and a mixture thereof.

The fatty alcohol may be saturated or unsaturated. Exemplary saturated liquid fatty alcohols may be branched and optionally contain in their structure at least one aromatic or non-aromatic ring. In some instances, however, the fatty alcohols are acyclic. Non-limiting examples of liquid saturated fatty alcohols include octyldodecanol, isostearyl alcohol, and 2-hexyldecanol.

Exemplary unsaturated liquid fatty alcohol may include in their structure at least one double or triple bond. For example, the fatty alcohols may include several double bonds (such as 2 or 3 double bond), which may be conjugated or non-conjugated. The unsaturated fatty alcohols can be linear or branched and may be acyclic or include in their structure at least one aromatic or non-aromatic ring. Liquid unsaturated fatty alcohols may include or be chosen from oleyl alcohol, linoleyl alcohol, linolenyl alcohol and undecylenyl alcohol.

The fatty alcohols may be alkoxylated fatty alcohols, e.g., having about 1 to about 100 moles of an alkylene oxide per mole of alkoxylated fatty alcohol. For example, the alkoxylated fatty alcohols may be alkoxylated with about 1 to about 80 moles, about 2 to about 50, about 5 to about 45 moles, about 10 to about 40 moles, or 15 to about 35 mores, including all ranges and subranges therebetween, of an alkylene oxide per mole of alkoxylated fatty alcohol.

As examples of alkoxylated fatty alcohols, steareth (for example, steareth-2, steareth-20, and steareth-21), laureth (for example, laureth-4, and laureth-12), ceteth (for example, ceteth-10 and ceteth-20) and ceteareth (for example, ceteareth-2, ceteareth-10, and ceteareth-20) are mentioned. In at least one instance, the one or more alkoxylated fatty alcohols include steareth-20. In some instances, the one or more alkoxylated fatty alcohols may be exclusively steareth-20.

Additional fatty alcohol derivatives that may, optionally be suitable include methyl stearyl ether; 2-ethylhexyl dodecyl ether; stearyl acetate; cetyl propionate; the ceteth series of compounds, such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

In some embodiments, the fatty alcohol is selected from cetearyl alcohol, cetyl alcohol, stearyl alcohol, behenyl alcohol, arachidyl alcohol, eicosyl alcohol, myristyl alcohol, 2-dodecylhexadecanol, 2-tetradecyl-1-octadecanol, 2-tetradecyl-1-eicosanol, 2-hexadecyl-1-octadecanol, 2-hexadecyl-1-eicosanol, and a mixture thereof. Preferably, the fatty alcohol is selected from cetearyl alcohol, cetyl alcohol, stearyl alcohol, and a mixture thereof.

Glucamide(s)

The hair cleansing composition includes one or more glucamide(s), typically, in an amount of about 1.5 to about 3 wt. %, based on the total weight of the hair cleansing composition. In some instances, the amount of glucamide(s) in the hair cleansing composition is about 1.5 to about 3 wt. %, about 1.5 to about 2.8 wt. %, about 1.5 to about 2.6 wt. %, about 1.5 to about 2.5 wt. %, about 1.5 to about 2.4 wt. %, about 1.5 to about 2.3 wt. %, about 1.5 to about 2.2 wt. %, or about 1.5 to about 2.1 wt. %; about 1.7 to about 3 wt. %, about 1.7 to about 2.8 wt. %, about 1.7 to about 2.6 wt. %, about 1.7 to about 2.5 wt. %, about 1.7 to about 2.4 wt. %, about 1.7 to about 2.3 wt. %, about 1.7 to about 2.2 wt. %, or about 1.7 to about 2.1 wt. %; about 1.9 to about 3 wt. %, about 1.9 to about 2.8 wt. %, about 1.9 to about 2.6 wt. %, about 1.9 to about 2.5 wt. %, about 1.9 to about 2.4 wt. %, about 1.9 to about 2.3 wt. %, about 1.9 to about 2.2 wt. %, or about 1.9 to about 2.1 wt. %, including ranges and sub-ranges therebetween, based on the total weight of the hair cleansing composition.

The glucamide may be an acyl glucamides. For example, the glucamide(s) may be selected from acyl glucamides having a carbon chain length of 8 to 20. Non-limiting examples include lauroyl/myristoyl methyl glucamide, capryloyl/capryl methyl glucamide, lauroyl methyl glucamide, myristoyl methyl glucamide, capryloyl methyl glucamide, capryl methyl glucamide, cocoyl methyl glucamide, capryloyl/caproyl methyl glucamide, cocoyl methyl glucamide, lauryl methylglucamide, oleoyl methylglucamide oleate, stearoyl methylglucamide stearate, sunfloweroyl methylglucamide, and tocopheryl succinate methylglucamide. The glucamide may be a $C_{10}$-$C_{18}$ N-alkyl ($C_1$-$C_6$) polyhydroxy fatty acid amides, such as the $C_{12}$-$C_{18}$ N-methyl glucamides, as described for example in WO 92 06154 and U.S. Pat. No. 5,194,639, which are incorporated herein in their entireties for all purposes, and the N-alkoxy polyhydroxy fatty acid amides, such as $C_{10}$-$C_{18}$ N-(3-methoxypropyl) glucamide.

The glucamide may, optionally, be selected from fatty glucamide sulphates, such as those described in patent application DE 44 43 645, which is incorporated herein in its entirety for all purposes. In some instances, the glucomide of hair cleansing composition includes or is selected from cocoyl methyl glucamide, lauroyl/myristoyl methyl glucamide, lauroyl methyl glucamide, and/or myristoyl methyl glucamide.

Alkanolamide(s)

The hair cleansing composition includes one or more alkanolamide(s) that is not a glucamide as discussed above. Typically, the amount of alkanolamide present in the hair cleansing composition is about 1.5 to about 5.5 wt. %, based on the total weight of the hair cleansing composition. In some instances, the amount of alkanolamide(s) in the hair cleansing composition is about 1.5 to about 5 wt. %, about 1.5 to about 4.5 wt. %, about 1.5 to about 4 wt. %, about 1.5 to about 3.5 wt. %, about 1.5 to about 3 wt. %, about 1.5 to about 2.5 wt. %, or about 1.5 to about 2 wt. %; about 1.75 to about 5.5 wt. %, about 1.75 to about 5 wt. %, about 1.75 to about 4.5 wt. %, about 1.75 to about 4 wt. %, about 1.75 to about 3.5 wt. %, about 1.75 to about 3 wt. %, about 1.75 to about 2.5 wt. %, or about 1.75 to about 2 wt. %; about 1.9 to about 5.5 wt. %, about 1.9 to about 5 wt. %, about 1.9 to about 4.5 wt. %, about 1.9 to about 4 wt. %, about 1.9 to about 3.5 wt. %, about 1.9 to about 3 wt. %, or about 1.9 to about 2.5 wt. %; about 2.1 to about 5.5 wt. %, about 2.1 to about 5 wt. %, about 2.1 to about 4.5 wt. %, about 2.1 to about 4 wt. %, about 2.1 to about 3.5 wt. %, or about 2.1 to about 3 wt. %; about 2.5 to about 5.5 wt. %, about 2.5 to about 5 wt. %, about 2.5 to about 4.5 wt. %, about 2.5 to about 4 wt. %, about 2.5 to about 3.5 wt. %, or about 2.5 to about 3 wt. %, including ranges and sub-ranges therebetween, based on the total weight of the hair cleansing composition.

Non-limiting examples of alkanolamides include fatty acid alkanolamides. The fatty acid alkanolamides may be fatty acid monoalkanolamides or fatty acid dialkanolamides or fatty acid isoalkanolamides, and may have a $C_{2-8}$ hydroxyalkyl group (the $C_{2-8}$ chain can be substituted with one or more than one —OH group). Non-limiting examples include fatty acid diethanolamides (DEA) or fatty acid monoethanolamides (MEA), fatty acid monoisopropanolamides (MIPA), fatty acid diisopropanolamides (DIPA), and fatty acid glucamides (acyl glucamides).

Suitable fatty acid alkanolamides may, in some instances, include those formed by reacting an alkanolamine and a $C_6$-$C_{36}$ fatty acid. Examples include, but are not limited to: oleic acid diethanolamide, myristic acid monoethanolamide, soya fatty acids diethanolamide, stearic acid ethanolamide, oleic acid monoisopropanolamide, linoleic acid diethanolamide, stearic acid monoethanolamide (Stearamide MEA), behenic acid monoethanolamide, isostearic acid monoisopropanolamide (isostearamide MIPA), erucic acid diethanolamide, ricinoleic acid monoethanolamide, coconut fatty acid monoisopropanolamide (cocoamide MIPA), coconut acid monoethanolamide (Cocamide MEA), palm kernel fatty acid diethanolamide, coconut fatty acid diethanolamide, lauric diethanolamide, polyoxyethylene coconut fatty acid monoethanolamide, coconut fatty acid monoethanolamide, lauric monoethanolamide, lauric acid monoisopropanolamide (lauramide MIPA), myristic acid monoisopropanolamide (Myristamide MIPA), coconut fatty acid diisopropanolamide (cocamide DIPA), and mixtures thereof.

In some instances, the fatty acid alkanolamides preferably include cocamide MIPA, cocamide DEA, cocamide MEA, cocamide DIPA, and mixtures thereof. In particular, the fatty acid alkanolamide may be cocamide MIPA, which has been commercially available under the tradename EMPILAN from Innospec Active Chemicals.

Fatty acid alkanolamides include those of the following structure:

wherein $R_4$ is an alkyl chain of 4 to 20 carbon atoms ($R_4$ may be, for example, selected from lauric acid, coconut acid, palmitic acid, myristic acid, behenic acid, babassu fatty acid, isostearic acid, stearic acid, corn fatty acid, soy fatty acid, shea butter fatty acids, caprylic acid, capric acid, and mixtures thereof); wherein $R_5$ is selected from —$CH_2OH$, —$CH_2CH_2OH$, —$CH_2CH_2CH_2OH$, —$CH_2(CHOH)_4CH_2OH$, -benzyl, and mixtures thereof; and wherein $R_6$ is selected from —H, —$CH_3$, —$CH_2OH$, —$CH_2CH_3$, —$CH_2CH_2OH$, —$CH_2CH_2CH_2OH$, —$CH_2(CHOH)_4CH_2OH$, -benzyl, and mixtures thereof.

Additional Nonionic Surfactant(s)

The hair cleansing composition may optionally include one or more additional nonionic surfactants. If present, the additional nonionic surfactants may be included in the hair cleansing composition in an amount of about 0.1 to about 5 wt. %, about 0.1 to about 4.5 wt. %, about 0.1 to about 4 wt. %, about 0.1 to about 3.5 wt. %, about 0.1 to about 3 wt. %, about 0.1 to about 2.5 wt. %, about 0.1 to about 2 wt. %, or about 0.1 to about 1.5 wt. %; about 0.5 to about 5 wt. %, about 0.5 to about 4.5 wt. %, about 0.5 to about 4 wt. %, about 0.5 to about 3.5 wt. %, about 0.5 to about 3 wt. %, about 0.5 to about 2.5 wt. %, about 0.5 to about 2 wt. %, or about 0.5 to about 1.5 wt. %; about 1 to about 5 wt. %, about 1 to about 4.5 wt. %, about 1 to about 4 wt. %, about 1 to about 3.5 wt. %, about 1 to about 3 wt. %, about 1 to about 2.5 wt. %, about 1 to about 2 wt. %, or about 1 to about 1.5 wt. %; about 1.5 to about 5 wt. %, about 1.5 to about 4.5 wt. %, about 1.5 to about 4 wt. %, about 1.5 to about 3.5 wt. %, about 1.5 to about 3 wt. %, about 1.5 to about 2.5 wt. %, or about 1.5 to about 2 wt. %; about 1.75 to about 5 wt. %, about 1.75 to about 4.5 wt. %, about 1.75 to about 4 wt. %, about 1.75 to about 3.5 wt. %, about 1.75 to about 3 wt. %, about 1.75 to about 2.5 wt. %, or about 1.75 to about 2 wt. %; about 1.9 to about 5 wt. %, about 1.9 to about 4.5 wt. %, about 1.9 to about 4 wt. %, about 1.9 to about 3.5 wt. %, about 1.9 to about 3 wt. %, or about 1.9 to about 2.5 wt. %; about 2.1 to about 5 wt. %, about 2.1 to about 4.5 wt. %, about 2.1 to about 4 wt. %, about 2.1 to about 3.5 wt. %, or about 2.1 to about 3 wt. %; about 2.5 to about 5 wt. %, about 2.5 to about 4.5 wt. %, about 2.5 to about 4 wt. %, about 2.5 to about 3.5 wt. %, or about 2.5 to about 3 wt. %, including ranges and sub-ranges therebetween, based on the total weight of the hair cleansing composition.

Non-limiting examples of additional nonionic surfactants that may optionally form part of the plurality of nonionic surfactants include, but are not limited to, alkyl polyglucoside(s), sorbitan derivative(s), polyol ester(s), or the like.

Alkyl Polyglucoside(s)

In some embodiments, the one or more alkyl polyglucosides include those chosen from lauryl glucoside, octyl glucoside, decyl glucoside, coco glucoside, caprylyl/capryl glucoside, sodium lauryl glucose carboxylate, and a mixture thereof. In some cases, the alkyl polyglucosides includes or is chosen from lauryl glucoside. Additionally or alternatively, the alkyl polyglucosides may be chosen from glycerol ($C_6$-$C_{24}$)alkylpolyglycosides including, e.g., polyethoxylated fatty acid mono or diesters of glycerol ($C_6$-$C_{24}$) alkylpolyglycosides. Additional alkyl polyglucosides that may be suitably incorporated, in some instances, in the hair treatment composition includes alkyl polyglucosides having a structure according to the following formula:

$$R^1-O-(R^2O)_n-Z(x)$$

wherein $R^1$ is an alkyl group having 8-18 carbon atoms;
$R^2$ is an ethylene or propylene group;
Z is a saccharide group with 5 to 6 carbon atoms;
n is an integer from 0 to 10; and
x is an integer from 1 to 5.

Useful alkyl poly glucosides may, in some instances, include lauryl glucoside, octyl glucoside, decyl glucoside, coco glucoside, caprylyl/capryl glucoside, and sodium lauryl glucose carboxylate. Typically, the at least one alkyl poly glucoside compound is selected from the group consisting of lauryl glucoside, decyl glucoside and coco glucoside. In some instances, decyl glucoside is particularly preferred.

Sorbitan Derivative(s)

Suitable sorbitan derivatives that may be incorporated into the plurality of nonionic surfactants include those chosen from polysorbate-20 (POE(20) sorbitan monolaurate), polysorbate-21 (POE(4) sorbitan monolaurate), polysorbate-40 (POE(20) sorbitan monopalmitate), polysorbate-60 (POE(20) sorbitan monostearate), polysorbate-61 (POE (4) sorbitan monostearate), polysorbate-65 (POE(20) sorbitan tristearate), polysorbate-80 (POE(20)sorbitan monooleate), polysorbate-81 (POE(4) sorbitan monooleate), polysorbate 85 (POE(20) Sorbitan Trioleate), sorbitan isostearate, sorbitan monolaurate, sorbitan monooleate, sorbitan monopalmitate, sorbitan monostearate, sorbitan sesquioleate, sorbitan trioleate and sorbitan tristearate and a mixture thereof.

Additional and/or alternative sorbitan derivatives include sorbitan esters including, e.g., esters of $C_{16}$-$C_{22}$ fatty acid and of sorbitan that were formed by esterification, with sorbitol, of at least one fatty acid comprising at least one saturated or unsaturated linear alkyl chain respectively having from 16 to 22 carbon atoms. These esters can be chosen in particular from sorbitan stearates, behenates, arachidates, palmitates or oleates, and their mixtures. Examples of optional sorbitan esters include sorbitan monostearate (INCI name: Sorbitan stearate) sold by Croda under the name Span 60, the sorbitan tristearate sold by Croda under the name Span 65 V, the sorbitan monopalmitate (INCI name: Sorbitan palmitate) sold by Croda under the name Span 40, the sorbitan monooleate sold by Croda under the name Span 80 V or the sorbitan trioleate sold by Uniqema under the name Span 85 V. A preferable sorbitan ester is sorbitan tristearate.

Polyol Ester(s)

Non-limiting examples of polyol esters include those chosen from alkoxylated polyol esters. For instance, the alkoxylated polyol esters may be chosen from pegylated derivatives of propylene glycol oleate, propylene glycol caprylate/caprate, propylene glycol cocoate, propylene glycol stearate, and a mixture thereof. In certain embodiments, the alkoxylated polyol esters are chosen from PEG-55 propylene glycol oleate, PEG-6 propylene glycol caprylate/ caprate, PEG-8 propylene glycol cocoate, PEG-25 propylene glycol stearate, and PEG-120 propylene glycol stearate, and a mixture thereof. In some instances, the polyol ester is or includes PEG-55 propylene glycol oleate. Additionally and/or alternatively, the polyol esters may be chosen from ethoxylated fatty acid esters of sorbitan comprising from 2 to 30 mol of ethylene oxide.

In some cases, the polyol ester may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and mixtures thereof.

Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups, such as PEG-9 to PEG-50 laurate (as the INCI names: PEG-9 laurate to PEG-50 laurate); PEG-9 to PEG-50 palmitate (as the INCI names: PEG-9 palmitate to PEG-50 palmitate); PEG-9 to PEG-50 stearate (as the INCI names: PEG-9 stearate to PEG-50 stearate); PEG-9 to PEG-50 palmitostearate; PEG-9 to PEG-50 behenate (as the INCI names: PEG-9 behenate to PEG-50 behenate); polyethylene glycol 100 EO monostearate (INCI name: PEG-100 stearate); and mixtures thereof.

Sources of unsaturated polyol esters of glycerol include synthesized oils, natural oils (e.g., vegetable oils, algae oils, bacterial derived oils, and animal fats), combinations of these, and the like. Non-limiting examples of vegetable oils include Abyssinian oil, Almond oil, Apricot oil, Apricot Kernel oil, Argan oil, Avocado oil, Babassu oil, Baobab oil, Black Cumin oil, Black Currant oil, Borage oil, Camelina oil, Carinata oil, Canola oil, Castor oil, Cherry Kernel oil, Coconut oil, Corn oil, Cottonseed oil, Echium oil, Evening Primrose oil, Flax Seed oil, Grape Seed oil, Grapefruit Seed oil, Hazelnut oil, Hemp Seed oil, Jatropha oil, Jojoba oil, Kukui Nut oil, Linseed oil, Macadamia Nut oil, Meadowfoam Seed oil, Moringa oil, Neem oil, Olive oil, Palm oil, Palm Kernel oil, Peach Kernel oil, Peanut oil, Pecan oil, Pennycress oil, Perilla Seed oil, Pistachio oil, Pomegranate Seed oil, Pongamia oil, Pumpkin Seed oil, Raspberry oil, Red Palm Olein, Rice Bran oil, Rosehip oil, Safflower oil, Seabuckthorn Fruit oil, Sesame Seed oil, Shea Olein, Sunflower oil, Soybean oil, Tonka Bean oil, Tung oil, Walnut oil, Wheat Germ oil, High Oleoyl Soybean oil, High Oleoyl Sunflower oil, High Oleoyl Safflower oil, High Erucic Acid Rapeseed oil, combinations of these, and the like. Non-limiting examples of animal fats include lard, tallow, chicken fat, yellow grease, fish oil, emu oil, combinations of these, and the like. Non-limiting example of a synthesized oil includes tall oil, which is a byproduct of wood pulp manufacture. In some embodiments, the natural oil is refined, bleached, and/or deodorized.

The polyol esters may optionally be a natural polyol esters chosen from vegetable oil, an animal fat, an algae oil and mixtures thereof; and said synthetic polyol ester is derived from a material selected from the group consisting of ethylene glycol, propylene glycol, glycerol, polyglycerol, polyethylene glycol, polypropylene glycol, poly(tetramethylene ether) glycol, pentaerythritol, dipentaerythritol, tripentaerythritol, trimethylolpropane, neopentyl glycol, a sugar, in one aspect, sucrose, and mixtures thereof.

Additional non-limiting examples of nonionic surfactants that may optionally be used in the hair treatment composition include and/or may be chosen from alkanolamides; polyoxyalkylenated nonionic surfactants; polyglycerolated nonionic surfactants; ethoxylated fatty esters; alcohols, alpha-diols, alkylphenols and esters of fatty acids, being ethoxylated, propoxylated or glycerolated; copolymers of ethylene oxide and/or of propylene oxide; condensates of ethylene oxide and/or of propylene oxide with fatty alcohols; polyethoxylated fatty amides; ethoxylated oils from plant origin; fatty acid esters of sucrose; fatty acid esters of polyethylene glycol; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and mixtures thereof.

Oil(s)

The hair cleansing compositions include one or more oils typically in the amount of about 0.5 or more wt. %, based on the total weight of the hair cleansing composition. In some instances, the oils are in an amount ranging from about 0.5 to about 5 wt. %, about 0.5 to about 4.5 wt. %, about 0.5 to about 4 wt. %, about 0.5 to about 3.5 wt. %, about 0.5 to about 3 wt. %, about 0.5 to about 2.5 wt. %, about 0.5 to about 2.25 wt. %, about 0.5 to about 2 wt. %, about 0.5 to about 1.75 wt. %, about 0.5 to about 1.5 wt. %, about 0.5 to about 1.25 wt. %, or about 0.5 to about 1 wt. %; about 0.75 to about 5 wt. %, about 0.75 to about 4.5 wt. %, about 0.75 to about 4 wt. %, about 0.75 to about 3.5 wt. %, about 0.75 to about 3 wt. %, about 0.75 to about 2.5 wt. %, about 0.75 to about 2.25 wt. %, about 0.75 to about 2 wt. %, about 0.75 to about 1.75 wt. %, about 0.75 to about 1.5 wt. %, or about 0.75 to about 1.25 wt. %; about 1 to about 5 wt. %, about 1 to about 4.5 wt. %, about 1 to about 4 wt. %, about 1 to about 3.5 wt. %, about 1 to about 3 wt. %, about 1 to about 2.5 wt. %, about 1 to about 2.25 wt. %, about 1 to about 2 wt. %, about 1 to about 1.75 wt. %, about 1 to about 1.5 wt. %, including ranges and sub-ranges therebetween, based on the total weight of the hair cleansing composition.

The oil component of the NLCs is typically has melting temperature of less than 45° C., a molecular weight of at least 190, and a solubility in water of no greater than 1 part in 99 parts of water.

Non-limiting examples of include, but are not limited to, natural oils, such as coconut oil; hydrocarbons, such as mineral oil and hydrogenated polyisobutene; esters, such as $C_{12}$-$C_{15}$ alkyl benzoate; diesters, such as propylene dipelarganate; and triesters, such as glyceryl trioctanoate. Further examples of oils that may, optionally, be included in the hair treatment compositions include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isododecanol, polyglyceryl-3-diisostearate, castor oil, lanolin and lanolin derivatives, triisocetyl citrate, sorbitan sesquioleate, $C_{10}$-$C_{18}$ triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof.

The oils may be non-silicone oils. In some instances, the hair cleansing composition is free or substantially free of silicone oils. For example, the hair cleansing composition may have an amount of silicone oils that is less than 6 wt. %, preferably less than 5 wt. %, preferably less than 4 wt. %, preferably less than 3 wt. %, preferably less than 2 wt. %, preferably less than 1 wt. %, preferably less than 0.5 wt. %, and/or preferably less than 0.1 wt. %, based on the total weight of the hair cleansing composition.

The oils may, optionally, be chosen from non-synthetic oils. In some instances, the hair cleansing composition is free or substantially free of synthetic oils. For example, the hair cleansing composition may have an amount of synthetic oils that is less than 6 wt. %, preferably less than 5 wt. %, preferably less than 4 wt. %, preferably less than 3 wt. %, preferably less than 2 wt. %, preferably less than 1 wt. %, preferably less than 0.5 wt. %, and/or preferably less than 0.1 wt. %, based on the total weight of the hair cleansing composition.

Additionally or alternatively, the oil may be selected from plant based and/or vegetable oils. Non-limiting examples of plant-based or vegetable oils include acai oil, almond oil, aloe vera oil, andiroba oil, annatto oil, avocado oil, babassu oil, borage oil, brazil nut oil, buriti oil, camelina oil, coffee oil, copaiba oil, emu oil, passion fruit oil, almond oil, castor oil, coconut oil, grapeseed oil, jojoba oil, macadamia nut oil, rose hip oil, ajwain oil, angelic root oil, anise oil, aragan oil, asafetida, balsam oil, basil oil, bay oil, bergamot oil, black pepper essential oil, buchu oil, birch oil, camphor, cannabis oil, caraway oil, cardamom seed oil, carrot seed oil, chamomile oil, calamus root oil, cinnamon oil, citronella oil, clary sage, clove leaf oil, coffee, coriander, costmary oil, cranberry seed oil, cubeb, cumin oil, cypress, cypriol, curry leaf, davana oil, dill oil, elecampane, eucalyptus oil, fennel seed oil, fenugreek oil, fir, frankincense oil, galangal, geranium oil, ginger oil, goldenrod, grapefruit oil, grapeseed oil, henna oil, helichrysum, horseradish oil, hyssop, Idaho tansy, jasmine oil, juniper berry oil, lavender oil, lemon oil, lemongrass, marjoram, melaleuca, lemon balm oil, mountain savory, mugwort oil, mustard oil, myrrh oil, myrtle, neem tree oil, neroli, nutmeg, orange oil, oregano oil, orris oil, palo santo, parsley oil, patchouli oil, perilla oil, pennyroyal oil, peppermint oil, petitgrain, pine oil, plum oil, ravensara, red cedar, roman chamomile, rose oil, rosehip oil, rosemary oil, rosewood oil, sandalwood oil, sassafras oil, savory oil, schisandra oil, spikenard, spruce, star anise oil, tangerine, tarragon oil, tea tree oil, thyme oil, tsuga oil, turmeric, valerian, vetiver oil, western red cedar, wintergreen, yarrow oil, ylang-ylang, and zedoary oil.

The oils may be a plant based oils, such as perhydrosqualene, liquid triglycerides of fatty acids comprising from 4 to 10 carbon atoms, such as heptanoic or octanoic acid triglycerides, or alternatively, for example, sunflower oil, maize oil, soybean oil, marrow oil, grapeseed oil, sesame seed oil, hazelnut oil, apricot kernel oil, macadamia oil, arara oil, coriander oil, castor oil, avocado oil, caprylic/capric acid triglycerides, such as those sold by the company Stearineries Dubois or those sold under the names MIGLYOL 810, 812 and 818 by the company Dynamit Nobel, jojoba oil and shea butter oil Non-limiting examples of liquid triglycerides and oils of plant origin include alexandria laurel tree oil, avocado oil, apricot stone oil, barley oil, borage seed oil, calendula oil, canelle nut tree oil, canola oil, caprylic/capric triglyceride castor oil, coconut oil, corn oil, cotton oil, cottonseed oil, evening primrose oil, flaxseed oil, groundnut oil, hazelnut oil, glycereth triacetate, glycerol triheptanoate, glyceryl trioctanoate, glyceryl triundecanoate, hempseed oil, jojoba oil, lucerne oil, maize germ oil, marrow oil, millet oil, neopentylglycol dicaprylate/dicaprate, olive oil, palm oil, passionflower oil, pentaerythrityl tetrastearate, poppy oil, propylene glycol ricinoleate, rapeseed oil, rye oil, safflower oil, sesame oil, shea butter, soya oil, soybean oil, sweet almond oil, sunflower oil, sysymbrium oil, syzigium aromaticum oil, tea tree oil, walnut oil, wheat germ glycerides and wheat germ oil.

In some instances, the oil is a plant oil selected from palm oil, soybean oil, olive oil, coconut oil, and a mixture thereof. In at least one embodiment, the oil the plant based oil includes at least coconut oil.

Cationic Polymer(s)

The hair cleansing compositions may include one or more cationic polymers. The amount of cationic polymers in the hair treatment composition typically ranges from about 0.01 to about 10 wt. % of the total weight of the hair treatment composition. In some instances, the conditioning agents are in an amount ranging from about 0.01 to about 10 wt. %, about 0.01 to about 8 wt. %, about 0.01 to about 6 wt. %, about 0.01 to about 5 wt. %, about 0.01 to about 4 wt. %, about 0.01 to about 3 wt. %, about 0.01 to about 2 wt. %, about 0.01 to about 1 wt. %; about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.25 to about 10 wt. %, about 0.25 to about 8 wt. %, about 0.25 to about 6 wt. %, about 0.25 to about 5 wt. %, about 0.25 to about 4 wt. %, about 0.25 to about 3 wt. %, about 0.25 to about 2 wt. %, about 0.25 to about 1 wt. %; about 0.5 to about 10 wt. %, about 0.5 to about 8 wt. %, about 0.5 to about 6 wt. %, about 0.5 to about 5 wt. %; about 1 to about 10 wt. %, about 1 to about 8 wt. %, about 1 to about 6 wt. %, about 1 to about 5 wt. %; about 2 to about 10 wt. %, about 2 to about 8 wt. %, about 2 to about 6 wt. %, or about 2 to about 5 wt. %, including ranges and sub-ranges therebetween, based on the total weight of the hair treatment composition.

The cationic polymers can comprise mixtures of monomer units derived from amine- and/or quaternary ammonium-substituted monomer and/or compatible spacer monomers. Suitable cationic polymers include, for example: copolymers of 1-vinyl-2-pyrrolidine and 1-vinyl-3-methyl-imidazolium salt (e.g., chloride salt) (referred to as Polyquaternium-16) such as those commercially available from BASF under the LUVIQUAT tradename (e.g., LUVIQUAT FC 370); copolymers of 1-vinyl-2-pyrrolidine and dimethylaminoethyl methacrylate (referred to as Polyquaternium-11) such as those commercially from Gar Corporation (Wayne, N.J., USA) under the GAFQUAT tradename (e.g., GAFQUAT 755N); and cationic diallyl quaternary ammonium-containing polymer including, for example, dimethyldiallyammonium chloride homopolymer and copolymers of acrylamide and dimethyldiallyammonium chloride (referred to as Polyquaternium-6 and Polyquaternium-7).

Other cationic polymers that may be used include polysaccharide polymers, such as cationic cellulose derivatives and cationic starch derivatives. Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide (referred to as Polyquaternium-10). Another type of cationic cellulose includes the polymeric quaternary ammonium salts of hydroxyethyl cellulose reacted with lauryl dimethyl ammonium-substituted epoxide (referred to as Polyquaternium-24). These materials are available from Amerchol Corp. (Edison, N.J., USA) under the tradename Polymer LM-200. Additionally or alternatively, the cationic conditioning polymers may include or be chosen from cationic guar gum derivatives, such as guar hydroxypropyltrimonium chloride.

The hair treatment composition may include or be chosen from polyquaterniums. For example, the hair treatment composition may include Polyquaternium-1 (ethanol, 2,2',2"-nitrilotris-, polymer with 1,4-dichloro-2-butene and N,N,N',N'-tetramethyl-2-butene-1,4-diamine), Polyquaternium-2, (poly[bis(2-chloroethyl) ether-alt-1,3-bis[3-(dimethylamino)propyl]urea]), Polyquaternium-4, (hydroxyethyl cellulose dimethyl diallylammonium chloride copolymer; Diallyldimethylammonium chloride-hydroxyethyl cellulose copolymer), Polyquaternium-5 (copolymer of acrylamide and quaternized dimethylammoniumethyl methacrylate), Polyquaternium-6 (poly(diallyldimethylammonium chloride)), Polyquaternium-7 (copolymer of acrylamide and diallyldimethylammonium chloride), Polyquaternium-8 (copolymer of methyl and stearyl dimethylaminoethyl ester of methacrylic acid, quaternized with dimethylsulphate), Polyquaternium-9 (homopolymer of N,N-(dimethylamino)ethyl ester of methacrylic acid, quaternized with bromomethane), Polyquaternium-10 (quaternized hydroxyethyl cellulose), Polyquaternium-11 (copolymer of vinylpyrrolidone and quaternized dimethylaminoethyl methacrylate), Polyquaternium-12 (ethyl methacrylate/abietyl methacrylate/diethylaminoethyl methacrylate copolymer quaternized with dimethyl sulfate), Polyquaternium-13 (ethyl methacrylate/oleyl methacrylate/diethylaminoethyl methacrylate copolymer quaternized with dimethyl sulfate), Polyquaternium-14 (trimethylaminoethylmethacrylate homopolymer), Polyquaternium-15 (acrylamide-dimethylaminoethyl methacrylate methyl chloride copolymer), Polyquaternium-16 (copolymer of vinylpyrrolidone and quaternized vinylimidazole), Polyquaternium-17 (adipic acid, dimethylaminopropylamine and dichloroethylether copolymer), Polyquaternium-18 (azelanic acid, dimethylaminopropylamine and dichloroethylether copolymer), Polyquaternium-19 (copolymer of polyvinyl alcohol and 2,3-epoxypropylamine), Polyquaternium-20 (copolymer of polyvinyl octadecyl ether and 2,3-epoxypropylamine), Polyquaternium-22 (copolymer of acrylic acid and diallyldimethylammonium chloride), Polyquaternium-24 (auaternary ammonium salt of hydroxyethyl cellulose reacted with a lauryl dimethyl ammonium substituted epoxide), Polyquaternium-27 (block copolymer of Polyquaternium-2 and Polyquaternium-17), Polyquaternium-28 (copolymer of vinylpyrrolidone and methacrylamidopropyl trimethylammonium), Polyquaternium-29 (chitosan modified with propylen oxide and quaternized with epichlorhydrin), Polyquaternium-30 (ethanaminium, N-(carboxymethyl)-N,N-dimethyl-2-[(2-methyl-1-oxo-2-propen-1-yl)oxy]-, inner salt, polymer with methyl 2-methyl-2-propenoate), Polyquaternium-31 (N,N-dimethylaminopropyl-N-acrylamidine quatemized with diethylsulfate bound to a block of polyacrylonitrile), Polyquaternium-32 (poly(acrylamide 2-methacryloxyethyltrimethyl ammonium chloride)), Polyquaternium-33 (copolymer of trimethylaminoethylacrylate salt and acrylamide), Polyquaternium-34 (copolymer of 1,3-dibromopropane and N,N-diethyl-N',N'-dimethyl-1,3-propanediamine), Polyquaternium-35 (methosulphate of the copolymer of methacryloyloxyethyltrimethylammonium and of methacryloyloxyethyldimethylacetylammonium), Polyquaternium-36 (copolymer of N,N-dimethylaminoethylmethacrylate and buthylmethacrylate, quaternized with dimethylsulphate), Polyquaternium-37 (poly(2-methacryloxyethyltrimethylammonium chloride)), Polyquaternium-39 (terpolymer of acrylic acid, acrylamide and diallyldimethylammonium Chloride), Polyquaternium-42 (poly[oxyethylene(dimethylimino)ethylene (dimethylimino)ethylene dichloride]), Polyquaternium-43 (copolymer of acrylamide, acrylamidopropyltrimonium chloride, 2-amidopropylacrylamide sulfonate and dimethylaminopropylamine), Polyquaternium-44 (3-Methyl-1-vinylimidazolium methyl sulfate-N-vinylpyrrolidone copolymer), Polyquaternium-45 (copolymer of (N-methyl-N-ethoxyglycine)methacrylate and N,N-dimethylaminoethylmethacrylate, quaternized with dimethyl sulphate), Polyquaternium-46 (terpolymer of vinylcaprolactam, vinylpyrrolidone, and quaternized vinylimidazole), Polyquaternium-47 (terpolymer of acrylic acid, methacrylamidopropyl trimethylammonium chloride, and methyl acrylate), and/or Polyquaternium-67.

In some instances, the hair treatment compositions of the instant disclosure include one or more cationic polymers selected from cationic cellulose derivatives, quaternized hydroxyethyl cellulose (e.g., polyquaternium-10), cationic starch derivatives, cationic guar gum derivatives, copolymers of acrylamide and dimethyldiallyammonium chloride (e.g., polyquaternium-7), polyquaterniums, and a mixture thereof. For example, the cationic polymer(s) may be selected from polyquaterniums, for example, polyquaterniums selected from polyquaternium-4, polyquaternium-5, polyquaternium-6, polyquaternium-7, polyquaternium-10, polyquaternium-22, polyquaternium-37, polyquaternium-39, polyquaternium-47, polyquaternium-53, polyquaternium-67 and a mixture thereof. A combination of two or more polyquaterniums can be useful.

In one instance, the one or more cationic polymers is chosen from polyquaternium 4, polyquaternium 6, polyquaternium 7, polyquaternium 10, polyquaternium 11, polyquaternium 16, polyquaternium 22, polyquaternium 28, polyquaternium 32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, guar hydroxypropyltrimonium chloride, and a mixture thereof.

Silicone(s)

The hair cleansing compositions may include one or more silicones. The total amount of the one or more silicones can vary but is typically from about 0.01 to about 15 wt. %, based on the total weight of the hair cleansing composition. The total amount of the silicones may be from about 0.01 to about 15 wt. %, about 0.01 to about 12 wt. %, about 0.01 to about 10 wt. %, about 0.01 to about 8 wt. %, about 0.01 to about 6 wt. %, about 0.01 to about 5 wt. %, about 0.01 to about 4 wt. %, about 0.01 to about 3 wt. %, about 0.01 to about 2 wt. %, about 0.01 to about 1 wt. %; about 0.1 to about 15 wt. %, about 0.1 to about 12 wt. %, about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.25 to about 15 wt. %, about 0.25 to about 12 wt. %, about 0.25 to about 10 wt. %, about 0.25 to about 8 wt. %, about 0.25 to about 6 wt. %, about 0.25 to about 5 wt. %, about 0.25 to about 4 wt. %, about 0.25 to about 3 wt. %, about 0.25 to about 2 wt. %, about 0.25 to about 1 wt. %; about 0.5 to about 15 wt. %, about 0.5 to about 12 wt. %, about 0.5 to about 10 wt. %, about 0.5 to about 8 wt. %, about 0.5 to about 6 wt. %, about 0.5 to about 5 wt. %; about 1 to about 15 wt. %, about 1 to about 12 wt. %, about 1 to about 10 wt. %, about 1 to about 8 wt. %, about 1 to about 6 wt. %, about 1 to about 5 wt. %; about 2 to about 15 wt. %, about 2 to about 12 wt. %, about 2 to about 10 wt. %, about 2 to about 8 wt. %, about 2 to about 6 wt. %, or about 2 to about 5 wt. %, including ranges and sub-ranges therebetween, based on the total weight of the hair cleansing compositions.

The silicones may be hydrophobic or, in some instances, be functionalized to be hydrophilic. Preferably, the silicones of the hair treatment compositions are amino functionalized silicone. The term "amino-functionalized silicone" means a silicone containing at least one primary amino, secondary amino, tertiary amino and/or quaternary ammonium group. The structure of the amino-functionalized silicone may be linear or branched, cyclic or non-cyclic. The amino functional group may be at any position in the silicone molecule, preferably at the end of the backbone (for example, in the case of amodimethicones) and/or in the side chain.

In some instances, the silicones silicone may be an amino silicone selected from amodimethicone, aminoethylaminopropyl dimethicone, aminopropyl dimethicone, and a mixture thereof.

In other instances, the amino-functionalized silicones are selected from compounds of the following formula:

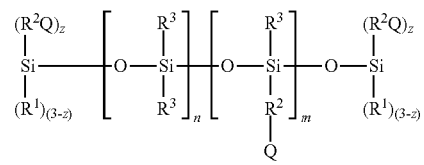

wherein each $R^1$ is independently selected from a $C_{1-30}$ alkyl group, a $C_{1-30}$ alkoxy group, a $C_{5-30}$ aryl group, a $C_{6-30}$ aralkyl group, a $C_{6-30}$ aralkyloxy group, a $C_{1-30}$ alkaryl group, a $C_{1-30}$ alkoxyaryl group, and a hydroxy group (preferably, each $R^1$ is independently selected from a $C_{1-30}$ alkyl group, a $C_{1-30}$ alkoxy group and a hydroxy group);

each $R^2$ is independently a divalent alkylene radical having one to ten carbon atoms (preferably, $R^2$ is a divalent alkylene radical having three to six carbon atoms);

each $R^3$ is independently selected from a $C_{1-30}$ alkyl group, a $C_{5-30}$ aryl group, a $C_{6-30}$ aralkyl group and a $C_{1-30}$ alkaryl group (preferably, each $R^3$ is independently selected from of a $C_{1-30}$ alkyl group);

Q is a monovalent radical selected from —$NR^4{}_2$ and —$NR^4(CH_2)_xNR^4{}_2$;

each $R^4$ is independently selected from a hydrogen and a $C_{1-4}$ alkyl group;

x is 2 to 6;

z is 0 or 1;

n is 25 to 3,000 (preferably, 25 to 2,000; more preferably, 25 to 1,000; most preferably 25 to 500); and m is 0 to 3,000 (preferably, 0 to 2,000; more preferably, 0 to 1,000; most preferably, 0 to 100);

with the proviso that at least 50 mol % of the total number of $R^1$ and $R^3$ groups are methyl and with the proviso that when m is 0, z is 1.

Preferred $R^1$ groups include methyl, methoxy, ethyl, ethoxy, propyl, propoxy, isopropyl, isopropoxy, butyl, butoxy, isobutyl, isobutoxy, phenyl, xenyl, benzyl, phenylethyl, tolyl and hydoxy. Preferred $R^2$ divalent alkylene radicals include trimethylene, tetramethylene, pentamethylene, —$CH_2CH(CH_3)CH_2$— and —$CH_2CH_2CH(CH_3)CH_2$—. Preferred $R^3$ groups include methyl, ethyl, propyl, isopropyl, butyl, isobutyl, phenyl, xenyl, benzyl, phenylethyl and tolyl. Preferred $R^4$ groups include methyl, ethyl, propyl, isopropyl, butyl and isobutyl. When z is 0, the amino-functionalized silicone has only pendant amine functional substituents in the polymer chain. When z is 1, the amino-functional silicone may have only terminal amine functional substituents (e.g., m=0) or may have both terminal and pendant amine functional substituents in the polymer chain (e.g., m>0). Preferably, n+m is 50 to 1,000. More preferably, n+m is 50 to 750. Still more preferably, n+m is 50 to 500. Most preferably, n+m is 50 to 250.

In some instances, the amino-functionalized silicones are alkoxylated and/or hydroxylated amino silicones. Suitable alkoxylated and/or hydroxylated amino silicones may be selected from compounds having a structure in accordance with the following formula:

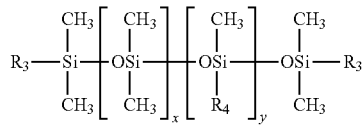

wherein $R_3$ is hydroxyl or $OR_5$, $R_5$ is a $C_1$ to $C_4$ alkyl group, $R_4$ is a group with a structure according to the following formula:

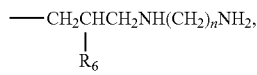

wherein $R_6$ is a $C_1$ to $C_4$ alkyl, n is a 1 to 4, x is the same as "n" described above, and y is the same as "m" described above.

Non-limiting examples of amino-functionalized silicones include bis-hydroxy/methoxy amodimethicones, bis-cetearyl amodimethicone, amodimethicone, bis(C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, and a mixture thereof. In some instances, a particularly useful amino-functionalized silicone is bis-hydroxy/methoxy amodimethicone, wherein X is isobutyl and one of the R is OH and the other is $OCH_3$ in the above structure, also known as "Bis-Hydroxy/Methoxy Amodimethicone" and "3-[(2-aminoethyl)amino]-2-methylpropyl Me, di-Me, [(hydroxydimethylsilyl)oxy]- and [methoxydimethylsilyl)oxy]terminated." Bis-hydroxy/methoxy amodimethicone is commercially available under the tradename DOWSIL AP-8087 FLUID from The Dow Chemical Company.

The silicone of the hair treatment composition may, in some instances, include polydiorganosiloxanes, e.g., polydimethylsiloxanes having the CTFA designation dimethicone. Additional silicones that may be suitable for the hair treatment compositions include (particularly for shampoos and conditioners) polydimethyl siloxanes having hydroxyl end groups, which have the CTFA designation dimethiconol. Silicone gums may, in some instances, be included in the hair treatment compositions, such as those having a slight degree of cross-linking. Non-limiting examples of silicone gums that may, optionally, be included are described in WO 96/31188, which is incorporated herein by reference for all purposes.

The silicone(s) may have a viscosity of at least 10,000 cst, such as at least 50,000 cst, at least 100,000 cst, at least 200,000 cst, at least 400,000 cst, at least 800,000 cst, at least 1,000,000 cst, or at least 2,000,000 cst. Preferably the viscosity does not exceed $10^9$ cst for ease of formulation.

The hair treatment composition may include pre-formed emulsions of silicones, such as emulsions DC2-1766, DC2-1784, and microemulsions DC2-1865 and DC2-1870 from Dow Corning, or cross-linked silicone gums, such as DC X2-1787 or DC X2-1391 from Dow Corning.

Fatty Compound(s)

The hair cleansing composition may include one or more fatty compounds. The amount of fatty compounds, if present, may vary but typically ranges from about 0.5 to about 20 wt. %, based on the total weight of the hair treatment composition. For example, the amount of fatty compounds, if present, in the hair cleansing composition may range from about 0.5 to about 18 wt. %, about 0.5 to about 16 wt. %, about 0.5 to about 14 wt. %, about 0.5 to about 12 wt. %, about 0.5 to about 10 wt. %, or about 0.5 to about 8 wt. %; about 1 to about 20 wt. %, about 1 to about 18 wt. %, about 1 to about 16 wt. %, about 1 to about 14 wt. %, about 1 to about 12 wt. %, about 1 to about 10 wt. %, or about 1 to about 8 wt. %; about 2 to about 20 wt. %, about 2 to about 18 wt. %, about 2 to about 16 wt. %, about 2 to about 14 wt. %, about 2 to about 12 wt. %, about 2 to about 10 wt. %, or about 2 to about 8 wt. %; about 3 to about 20 wt. %, about 3 to about 18 wt. %, about 3 to about 16 wt. %, about 3 to about 14 wt. %, about 3 to about 12 wt. %, about 3 to about 10 wt. %, or about 3 to about 8 wt. %; about 4 to about 20 wt. %, about 4 to about 18 wt. %, about 4 to about 16 wt. %, about 4 to about 14 wt. %, about 4 to about 12 wt. %, about 4 to about 10 wt. %, or about 4 to about 8 wt. %; about 5 to about 20 wt. %, about 5 to about 18 wt. %, about 5 to about 16 wt. %, about 5 to about 14 wt. %, about 5 to about 12 wt. %, about 5 to about 10 wt. %, or about 5 to about 8 wt. %, including all ranges and sub-ranges therebetween, based on the total weight of the hair cleansing composition.

The fatty compounds may optionally include or may be chosen from alkanes (paraffins), fatty acids, fatty alcohol derivatives, fatty acid derivatives, esters of fatty alcohols, hydroxy-substituted fatty acids, waxes, lanolin, and a mixture thereof.

Fatty compounds may include or be chosen from one of the following fatty acids or waxes if not falling within one of the foregoing groups.

Fatty Acid(s)

In some instances, the fatty compounds may optionally be chosen from fatty acids, fatty acid derivatives, esters of fatty acids, hydroxyl-substituted fatty acids, and alkoxylated fatty acids. The fatty acids may be straight or branched chain acids and/or may be saturated or unsaturated. Non-limiting examples of fatty acids include diacids, triacids, and other multiple acids as well as salts of these fatty acids. For example, the fatty acid may optionally include or be chosen from lauric acid, palmitic acid, stearic acid, behenic acid, arichidonic acid, oleic acid, isostearic acid, sebacic acid, and a mixture thereof. The fatty acids may be selected from the group consisting of palmitic acid, stearic acid, and a mixture thereof.

Non-limiting examples of polyglycerol esters of fatty acids include those of the following formula:

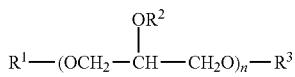

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols described above, hydroxy-substituted fatty acids, and a mixture thereof. Non-limiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

Wax(es)

The fatty compounds may, in some instances, include one or more waxes. Non-limiting examples of waxes in this category include for example, synthetic wax, ceresin, paraffin, ozokerite, polyethylene waxes, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, acacia decurrents flower wax, vegetable waxes (such as sunflower seed (Helianthus annuus), carnauba, candelilla, ouricury or japan wax or cork fibre or sugarcane waxes), or a mixture thereof.

Additional aspects of the disclosure relate to methods of preparing and using such hair cleansing compositions. A method for cleaning hair typically includes:

(a) applying the hair cleansing composition to hair; and (b) rinsing the hair for removing the hair cleansing composition.

Although the hair cleansing composition is typically applied while the hair is wet (e.g., while the user is taking a shower or bath), the hair cleansing composition may be applied when the hair is damp or dry. The hair cleansing composition may be retained on the hair for 1 or more, 2 or more, 5 or more, 10 or more, or 20 or more minutes. Typically, the hair cleansing composition is rinsed off after 1 hour or less, 45 minutes or less, 30 minutes or less, 20 minutes or less, 10 minutes or less, 5 minutes or less, 2 minutes or less, or 1 minute or less.

The hair cleansing composition may be applied to the hair individually or may be combined with one or more additional compositions. In some cases, the method includes applying a conditioner after rinsing off the hair cleansing composition. In other cases, the method includes applying a conditioner before rinsing off the hair cleansing composition.

Combining the hair cleansing with one or more additional compositions (e.g., a conditioner, a rinse, etc.) can be useful for eliminating multiple steps from a routine. For instance, the cosmetic composition may be mixed with a conditioner prior to application to the hair. In this case, the mixture of the conditioner and the hair cleansing composition are simultaneously applied to the hair during the cleansing or conditioning process and simultaneously rinsed from the hair. In at least one instance, conditioner may be layered on top of (or lathered into) hair to which the hair cleansing composition has already been applied or vice versa. For example, the hair cleansing composition may be applied to the hair and without rinsing it from the hair, a conditioner is then subsequently applied to the hair. Alternatively, the conditioner may be first applied to the hair and without rinsing the conditioner from the hair, the hair cleansing composition is also applied to the hair.

A typical method for preparing the hair cleansing compositions include:

(I) preparing a mixture comprising:

(a) about 8 to about 20 wt. % of an sulfate based anionic surfactant, (b) about 1 to about 4 wt. % of amphoteric surfactant, (c) about 4 to about 10 wt. % of a plurality of nonionic surfactants, the plurality of nonionic surfactants comprising:

(i) about 1 to about 1.5 wt. % of fatty alcohols, (ii) about 1.5 to about 3 wt. % of glucamide, and (iii) about 1.5 to about 5.5 wt. % of alkanolamide, (e) water, (II) applying heat to the mixture; and (III) adding (d) about 0.5 to 2.5 wt. % of an oil, wherein the oil is non-synthetic before or after applying heat to the mixture, wherein all weight percentages are based on the total weight of the prepared hair cleansing composition. The mixture of components (a) to (e) may be heated to a temperature of 30° C. or more, 40° C. or more, 50° C. or more, 60° C. or more, 70° C. or more, 80° C. or more, or 90° C. or more. Additional water may be added after heating of the mixture to attain a desired amount of water or other components based on a weight percentage of the total hair cleansing composition.

EMBODIMENTS

In certain embodiments, the hair cleansing compositions of the instant disclosure include:
- about 8 to about 20 wt. %, preferably about 8 to about 18 wt %, more preferably about 10 to about 16 wt. %, of a sulfate based anionic surfactant, such as those selected from sodium lauryl ether sulfate, sodium lauryl sulfate, ammonium lauryl ether sulfate, ammonium lauryl sulfate, and a mixture thereof;
- about 1 to about 4 wt. %, preferably about 1 to about 3 wt. %, more preferably about 1.25 to about 3 wt. %, of an amphoteric surfactant, wherein the amphoteric surfactant is selected from cocamidoethyl betaine, cocamidopropyl betaine, cocamidopropyl hydroxysultaine, cocamidopropyl dimethylamine propionate, cocoamphoglycinate, cocoamphocarboxypropionate, cocoamphocarboxyglycinate, coco-betaine, cocoamphopropionate, cocoamphopropylsulfonate, and a mixture thereof;
- about 4 to about 10 wt. %, preferably about 4 to about 9 wt. %, more preferably about 4 to about 6 wt. %, of a plurality of nonionic surfactants, the plurality of nonionic surfactants comprising:
  (i) about 1 to about 1.5 wt. %, preferably about 1 to about 1.4 wt. %, more preferably about 1 to about 1.3 wt. %, of a fatty alcohol, such as cetearyl alcohol, cetyl alcohol, stearyl alcohol, behenyl alcohol, arachidyl alcohol, eicosyl alcohol, myristyl alcohol, 2-dodecylhexadecanol, 2-tetradecyl-1-octadecanol, 2-tetradecyl-1-eicosanol, 2-hexadecyl-1-octadecanol, 2-hexadecyl-1-eicosanol, or a mixture thereof,
  (ii) about 1.5 to about 3 wt. %, preferably about 1.5 to about 2.5 wt. %, more preferably about 1.7 to about 2.5 wt. %, of a glucamide, preferably selected from lauroyl/myristoyl methyl glucamide, capryloyl/capryl methyl glucamide, lauroyl methyl glucamide, myristoyl methyl glucamide, capryloyl methyl glucamide, capryl methyl glucamide, cocoyl methyl glucamide, caproyl/caproyl methyl glucamide, cocoyl methyl glucamide, lauryl methylglucamide, oleoyl methylglucamide oleate, stearoyl methylglucamide stearate, sunfloweroyl methylglucamide, tocopheryl succinate methylglucamide, and a mixture thereof, and
  (iii) about 1.5 to about 5.5 wt. %, preferably about 1.5 to about 4.5 wt. %, more preferably about 1.5 to about 3 wt. %, of an alkanolamide that is not the glucamide, such as an alkanolamide selected from cocamide MEA, cocamide DEA, soyamide DEA, lauramide DEA, oleamide MIPA, stearamide MEA, myristamide DEA, stearamide DEA, oleylamide DEA, tallowamide DEA lauramide MIPA, tallowamide MEA, isostearamide DEA, isostearamide MEA, and a mixture thereof.
  wherein a weight ratio of an amount of the fatty alcohol of (i) to an amount of the glucamide of (ii) is, optionally, 1:1.3 to 1:2.5 or 1:1.5 to 1:2,
- about 0.5 to 2.5 wt. %, preferably about 0.5 to about 2 wt. %, more preferably about 0.5 to about 1.5 wt. %, of a non-silicone oil, wherein the non-silicone oil may be a plant based oil selected from coconut oil, soybean oil, canola oil, rapeseed oil, corn oil, cottonseed oil, olive oil, palm oil, peanut oil, safflower oil, sesame oil, sunflower oil, linseed oil, palm kernel oil, tung oil, jatropha oil, mustard oil, camelina oil, pennycress oil, castor oil, wheatgerm oil, apricot kernel oil, pistachio oil, poppy oil, pine oil, avocado oil, hazel nut oil, grapeseed oil, colza oil, cade oil, peach kernel oil, coffee bean oil, jojoba oil, and a mixture thereof.
- water, wherein all weight percentages are based on the total weight of the hair cleansing composition.

In additional embodiments, the hair cleansing compositions of the instant disclosure include:
- about 8 to about 20 wt. %, preferably about 8 to about 18 wt %, more preferably about 10 to about 16 wt. %, of a sulfate based anionic surfactant, such as those selected from sodium lauryl ether sulfate, sodium lauryl sulfate, ammonium lauryl ether sulfate, ammonium lauryl sulfate, and a mixture thereof;
- about 1 to about 2 wt. %, preferably about 1.25 to about 2 wt. %, of amphoteric surfactant, wherein the an amphoteric surfactant is selected from cocamidoethyl betaine, cocamidopropyl betaine, cocamidopropyl hydroxysultaine, cocamidopropyl dimethylamine propionate, cocoamphoglycinate, cocoamphocarboxypropionate, cocoamphocarboxyglycinate, coco-betaine, cocoamphopropionate, cocoamphopropylsulfonate, and a mixture thereof;
- about 4 to about 10 wt. %, preferably about 4 to about 9 wt. %, more preferably about 4 to about 6 wt. %, of a plurality of nonionic surfactants, the plurality of nonionic surfactants comprising:
  (i) about 1 to about 1.5 wt. %, preferably about 1 to about 1.4 wt. %, more preferably about 1 to about 1.3 wt. %, of a fatty alcohol, such as cetearyl alcohol, cetyl alcohol, stearyl alcohol, behenyl alcohol, arachidyl alcohol, eicosyl alcohol, myristyl alcohol, 2-dodecylhexadecanol, 2-tetradecyl-1-octadecanol, 2-tetradecyl-1-eicosanol, 2-hexadecyl-1-octadecanol, 2-hexadecyl-1-eicosanol, or a mixture thereof,
  (ii) about 1.5 to about 3 wt. %, preferably about 1.5 to about 2.5 wt. %, more preferably about 1.7 to about 2.5 wt. %, of a glucamide, preferably selected from lauroyl/myristoyl methyl glucamide, capryloyl/capryl methyl glucamide, lauroyl methyl glucamide, myristoyl methyl glucamide, capryloyl methyl glucamide, capryl methyl glucamide, cocoyl methyl glucamide, caproyl/caproyl methyl glucamide, cocoyl methyl glucamide, lauryl methylglucamide, oleoyl methylglucamide oleate, stearoyl methylglucamide stearate, sunfloweroyl methylglucamide, tocopheryl succinate methylglucamide, and a mixture thereof, and
  (iii) about 1.5 to about 5.5 wt. %, preferably about 1.5 to about 4.5 wt. %, more preferably about 1.5 to about 3 wt. %, of an alkanolamide that is not the glucamide, such as an alkanolamide selected from cocamide MEA, cocamide DEA, soyamide DEA, lauramide DEA, oleamide MIPA, stearamide MEA, myristamide DEA, stearamide DEA, oleylamide DEA, tallowamide DEA lauramide MIPA, tallowamide MEA, isostearamide DEA, isostearamide MEA, and a mixture thereof.
  wherein a weight ratio of an amount of the fatty alcohol of (i) to an amount of the glucamide of (ii) is 1:1.3 to 1:2.5, preferably 1:1.5 to 1:2,
- about 0.5 to 2.5 wt. %, preferably about 0.5 to about 2 wt. %, more preferably about 0.5 to about 1.5 wt. %, of a plant based oil, wherein the plant based oil comprises coconut oil.
- about 0.01 to about 3 wt. %, preferably about 0.01 to about 2 wt. %, more preferably about 0.1 to about 1 wt. %, of a cationic polymer, where the cationic polymer may be selected from selected from polyquaternium 4, polyquaternium 6, polyquaternium 7, polyquaternium 10, polyquaternium 11, polyquaternium 16, polyquaternium 22, polyquaternium 28, polyquaternium 32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, guar hydroxypropyltrimonium chloride, and a mixture thereof;

about 0.1 to about 5 wt. %, preferably 0.1 to about 3 wt. %, more preferably about 0.25 to about 2 wt. %, of a silicone, wherein the silicone is preferably selected from amodimethicone, aminoethylaminopropyl dimethicone, aminopropyl dimethicone, and a mixture thereof;

water, wherein all weight percentages are based on the total weight of the hair cleansing composition.

In further embodiments, a method for preparing a hair cleansing composition comprising:

(I) preparing a mixture comprising:

about 8 to about 20 wt. %, preferably about 8 to about 18 wt %, more preferably about 10 to about 16 wt. %, of a sulfate based anionic surfactant, such as sodium lauryl ether sulfate, sodium lauryl sulfate, ammonium lauryl ether sulfate, ammonium lauryl sulfate, or a mixture thereof;

about 1 to about 4 wt. %, preferably about 1 to about 3 wt. %, more preferably about 1.25 to about 3 wt. %, of an amphoteric surfactant, wherein the amphoteric surfactant is selected from cocamidoethyl betaine, cocamidopropyl betaine, cocamidopropyl hydroxysultaine, cocamidopropyl dimethylamine propionate, cocoamphoglycinate, cocoamphocarboxypropionate, cocoamphocarboxyglycinate, coco-betaine, cocoamphopropionate, cocoamphopropylsulfonate, and a mixture thereof;

about 4 to about 10 wt. %, preferably about 4 to about 9 wt. %, more preferably about 4 to about 6 wt. %, of a plurality of nonionic surfactants, the plurality of nonionic surfactants comprising:

(i) about 1 to about 1.5 wt. %, preferably about 1 to about 1.4 wt. %, more preferably about 1 to about 1.3 wt. %, of a fatty alcohol, such as cetearyl alcohol, cetyl alcohol, stearyl alcohol, behenyl alcohol, arachidyl alcohol, eicosyl alcohol, myristyl alcohol, 2-dodecylhexadecanol, 2-tetradecyl-1-octadecanol, 2-tetradecyl-1-eicosanol, 2-hexadecyl-1-octadecanol, 2-hexadecyl-1-eicosanol, or a mixture thereof, (ii) about 1.5 to about 3 wt. %, preferably about 1.5 to about 2.5 wt. %, more preferably about 1.7 to about 2.5 wt. %, of a glucamide, preferably selected from lauroyl/myristoyl methyl glucamide, capryloyl/capryl methyl glucamide, lauroyl methyl glucamide, myristoyl methyl glucamide, capryloyl methyl glucamide, capryl methyl glucamide, cocoyl methyl glucamide, capryloyl/caproyl methyl glucamide, cocoyl methyl glucamide, lauryl methylglucamide, oleoyl methylglucamide oleate, stearoyl methylglucamide stearate, sunfloweroyl methylglucamide, tocopheryl succinate methylglucamide, and a mixture thereof, and (iii) about 1.5 to about 5.5 wt. %, preferably about 1.5 to about 4.5 wt. %, more preferably about 1.5 to about 3 wt. %, of an alkanolamide that is not the glucamide, the alkanolamide selected from cocamide MEA, cocamide DEA, soyamide DEA, lauramide DEA, oleamide MIPA, stearamide MEA, myristamide DEA, stearamide DEA, oleylamide DEA, tallowamide DEA lauramide MIPA, tallowamide MEA, isostearamide DEA, isostearamide MEA, and a mixture thereof.

wherein a weight ratio of an amount of the fatty alcohols of (i) to an amount of the glucamide of (ii) is 1:1.3 to 1:2.5, preferably 1:1.5 to 1:2, about 0.5 to 2.5 wt. %, preferably about 0.5 to about 2 wt. %, more preferably about 0.5 to about 1.5 wt. %, of a non-silicone oil, wherein the non-silicone oil may be a plant based oil selected from coconut oil, soybean oil, canola oil, rapeseed oil, corn oil, cottonseed oil, olive oil, palm oil, peanut oil, safflower oil, sesame oil, sunflower oil, linseed oil, palm kernel oil, tung oil, jatropha oil, mustard oil, camelina oil, pennycress oil, castor oil, wheatgerm oil, apricot kernel oil, pistachio oil, poppy oil, pine oil, avocado oil, hazel nut oil, grapeseed oil, colza oil, cade oil, peach kernel oil, coffee bean oil, jojoba oil, and a mixture thereof.

(II) applying heat to the mixture; and (III) adding about 0.5 to 2.5 wt. % preferably about 0.5 to about 2 wt. %, more preferably about 0.5 to about 1.5 wt. %, of a non-silicone oil before or after applying heat to the mixture, wherein the non-silicone oil may be a plant based oil selected from coconut oil, soybean oil, canola oil, rapeseed oil, corn oil, cottonseed oil, olive oil, palm oil, peanut oil, safflower oil, sesame oil, sunflower oil, linseed oil, palm kernel oil, tung oil, jatropha oil, mustard oil, camelina oil, pennycress oil, castor oil, wheatgerm oil, apricot kernel oil, pistachio oil, poppy oil, pine oil, avocado oil, hazel nut oil, grapeseed oil, colza oil, cade oil, peach kernel oil, coffee bean oil, jojoba oil, and a mixture thereof, wherein all weight percentages are based on the total weight of the prepared hair cleansing composition.

Example 1

| | | INCI | Ex. A | Ex. B | Ex. C | Ex. D | Ex. E |
|---|---|---|---|---|---|---|---|
| (a) | Sulfate based anionic surfactant | SODIUM LAURYL SULFATE | 2.3 | 2.3 | 2.3 | 2.3 | 2.3 |
| | | SODIUM LAURETH SULFATE | 10.5 | 10.5 | 9.8 | 10.5 | 9.8 |
| (b) | Amphoteric surfactant | COCO-BETAINE | 1.5 | 1.5 | 1.5 | 1.5 | 1.5 |
| (c) | (i) Fatty alcohols | CETEARYL ALCOHOL | 1 | 1 | 1 | 1 | 1 |
| | (ii) Glucamide | LAUROYL/MYRISTOYL METHYL GLUCAMIDE | 1.91 | 1.91 | 1.53 | 1.91 | 1.53 |

-continued

| | INCI | Ex. A | Ex. B | Ex. C | Ex. D | Ex. E |
|---|---|---|---|---|---|---|
| | Weight ratio of fatty alcohols of (i) to glucamide of (ii) | 1:1.9 | 1:1.9 | 1:1.53 | 1:1.9 | 1:1.53 |
| (iii) Alkanolamide | COCAMIDE MEA | 1.5 | 1.5 | 1.8 | 1.5 | 1.8 |
| (iv) Nonionic surfactants | TRIDECETH-10, TRIDECETH-3, STEARETH-6, and PEG-100 STEARATE | <0.1 | <0.1 | <0.1 | <0.1 | <0.1 |
| (d) Oil | COCOS NUCIFERA (COCONUT) OIL | 0.5 | 0.5 | 0.5 | 0.5 | 0.5 |
| (f) Cationic polymer | POLYQUATERNIUM-7 and GUAR HYDROXYPROPYLTRIMONIUM CHLORIDE | 0.56 | 0.56 | 0.48 | 0.56 | 0.48 |
| (h) Silicone | DIMETHICONE and AMODIMETHICONE | 0.5 | 0.5 | 0.5 | 0.5 | 0.5 |
| Fragrance | FRAGRANCE | 1 | | | 1.2 | 1.2 |
| Salt | SODIUM CHLORIDE | 0.93 | 0.93 | 0.93 | 0.93 | 0.93 |
| Preservative | PHENOXYETHANOL, SALICYLIC ACID, and SODIUM BENZOATE | 0.7 | 0.7 | 0.7 | 0.7 | 0.7 |
| pH modifier | CITRIC ACID | 0.15 | 0.15 | 0.14 | 0.15 | 0.14 |
| Miscellaneous | FUMARIC ACID, SORBIC ACID, and ACETIC ACID | <0.1 | <0.1 | <0.1 | <0.1 | <0.1 |
| (e) Water | WATER | 77.4 | 78.4 | 79.3 | 77.2 | 78.1 |

Example 2

Exemplary Composition A was evaluated in comparison to a commercial benchmark composition (Commercial Benchmark A). The list of ingredients for Commercial Benchmark A are provided below:

Commercial Benchmark A: Water Sodium Lauryl Sulfate, Sodium Laureth Sulfate, Cocamidopropyl Betaine, Cetyl Alcohol, Stearyl Alcohol, Guar Hydroxypropyltrimonium Chloride, Dimethicone, Dimethiconol, Preservatives, and Fragrance.

Expert evaluators applied Exemplary Composition A and Commercial Benchmark A to 10 individuals for this evaluation. Specifically, the expert evaluators applied Exemplary Composition A to a first half of an individual's head of hair and applied Commercial Benchmark A to the second half of the individual's head of hair.

The expert evaluators ranked each side of the individuals' hair based on the properties mentioned below. Statistical analysis was then completed based on the evaluations using a PEC test and a N=10 model.

Exemplary Composition A exhibited slightly better results than Commercial Benchmark A for hair smoothness in foam, flash foam, ease of distribution during application, ease of combining while wet, smoothness of hair while wet, coating amount while hair is wet, ease of passing fingers through wet hair, detangling of hair while wet, suppleness of hair while dry, and combining of hair while dry. Commercial Benchmark A exhibited slightly better than Exemplary Composition A for squeaky cleanness, individualization of hair while wet, and hair body and individualization when dry.

Example 3

Exemplary Composition A was evaluated in comparison to a second commercial benchmark composition (Commercial Benchmark B). The list of ingredients for Commercial Benchmark B are provided below:

Commercial Benchmark B: Aqua/Water/Eau, Sodium lauroyl methyl isethionate, Sodium methyl cocoyl taurate, Coco-Betaine, Glycerin, Lauroyl/Myristoyl methyl glucamide, Opuntia ficus-indica (cactus) stem water, Opuntia ficus-indica (prickly pear) seed oil, Cocamidopropyl betaine, Cocamide DIPA, PEG-150 distearate, Citric acid, Polyquaternium-10, Polyquaternium-7, Polyquaternium-47, Trisodium ethylenediamine disuccinate, Tetrasodium EDTA, Magnesium nitrate, Sodium benzoate, Sodium chloride, Sodium acetate, Methylchloroisothiazolinone, Methylisothiazolinone, Magnesium chloride, Phenoxyethanol, Potassium sorbate, Parfum/Fragrance, Citronellol, Hexyl cinnamal, and Linalool.

An expert evaluator applied Exemplary composition A to a first half of an individual's head of hair and applied Commercial Benchmark B to the second half of the individual's head of hair. Exemplary Composition A and Commercial Benchmark B were applied to only 1 individual for this evaluation.

The expert evaluator ranked each side of the individual's hair based on the properties mentioned below. If Exemplary Composition A or Commercial Benchmark B exhibited "better" results than the other composition, a "✓" was given. If Exemplary Composition A or Commercial Benchmark B exhibited "noticeably better" results than the other composition, a "✓✓" was given.

TABLE 1

| Attributes | Exemplary Composition A | Commercial Benchmark B |
|---|---|---|
| Flash Foam | | ✓ |
| Distribution Ease | | ✓ |
| Smoothness in Foam | ✓✓ | |
| Movability | | ✓ |
| Abundance | | ✓ |
| Airy Foam | | ✓ |
| Foam stability | ✓ | |
| Speed of Rinse | | ✓ |
| Smoothness in rinse | ✓✓ | |
| Hair Feels Clean | | ✓ |
| Less tangles | ✓✓ | |

Exemplary Composition A exhibited "better" foam stability than Commercial Benchmark B. In addition, Exemplary Composition A exhibited "noticeably better" smoothness in foam, smoothness in rinse, and provided less tangling for the hair than Commercial Benchmark B.

Example 4

Exemplary Composition A was evaluated in comparison to a third commercial benchmark composition (Commercial Benchmark C). The list of ingredients for Commercial Benchmark C are provided below:

Commercial Benchmark C: Salicylic Acid, Water, Lauroyl/Myristoyl Methyl Glucamide, Decyl Glucoside, Coco-Betaine, Sodium Cocoyl Isethionate, Sodium Chloride, Sodium Hydroxide, Glycerin, Cocamide Mipa, Citric Acid, Brassicamidopropyl Dimethylamine, Hydrogenated Coconut Acid, Sorbic Acid, Sodium Isethionate, *Salix Alba* (Willow) Bark Extract, Sodium Phytate, *Rosmarinus Officinalis* (Rosemary) Leaf Extract, Alcohol, Sodium Benzoate, Lactic Acid, Potassium Sorbate.

An expert evaluator applied Exemplary composition A to a first half of an individual's head of hair and applied Commercial Benchmark C to the second half of the individual's head of hair. Exemplary Composition A and Commercial Benchmark C were applied to only 1 individual for this evaluation.

The expert evaluator ranked each side of the individual's hair based on the properties mentioned below. Table 2, shown below, provides the results of the statistical analysis of the individuals' evaluations. If Exemplary Composition A or Commercial Benchmark C exhibited "better" results than the other composition, a "✓" was given. If Exemplary Composition A or Commercial Benchmark B exhibited "noticeably better" results than the other composition, a "✓✓" was given.

TABLE 2

| Attributes | Exemplary Composition A | Commercial Benchmark C |
|---|---|---|
| Flash Foam | | ✓ |
| Distribution Ease | ✓ | |
| Smoothness in Foam | ✓ | |
| Movability | ✓✓ | |
| Abundance | ✓✓ | |
| Airy Foam | ✓✓ | |
| Foam stability | ✓ | |
| Speed of Rinse | ✓✓ | |
| Smoothness in rinse | ✓ | |
| Hair Feels Clean | | ✓ |
| Less tangles | ✓✓ | |

Exemplary Composition A exhibited "better" distribution ease, smoothness in foam, foam stability, and smoothness in rinse than Commercial Benchmark C. In addition, Exemplary Composition A exhibited "noticeably better" movability, abundance, airy foam, speed of rinse, and provided less tangling for the hair than Commercial Benchmark C.

Example 5

| | | INCI | Ex. B | Comp. A | Comp. B | Comp. C | Comp. D |
|---|---|---|---|---|---|---|---|
| (a) | Sulfate based anionic surfactant | SODIUM LAURYL SULFATE | 2.3 | 2.3 | 2.3 | 2.3 | 2.3 |
| | | SODIUM LAURETH SULFATE | 10.5 | 10.5 | 10.5 | 10.5 | 10.5 |
| (b) | Amphoteric surfactant | COCO-BETAINE | 1.5 | 1.5 | 1.5 | 1.5 | 1.5 |
| (c) | (i) Fatty alcohols | CETEARYL ALCOHOL | 1 | | | 1 | 1 |
| | (ii) Glucamide | LAUROYL/MYRISTOYL METHYL GLUCAMIDE | 1.91 | | 1.91 | 1.91 | |
| | Weight ratio of fatty alcohols of (i) to glucamide of (ii) | | 1:1.9 | | | 1:1.9 | |
| | (iii) Alkanolamide | COCAMIDE MEA | 1.5 | | 1.5 | | 1.5 |
| | (iv) Nonionic surfactants | TRIDECETH-10, TRIDECETH-3, STEARETH-6, and PEG-100 STEARATE | <0.1 | <0.1 | <0.1 | <0.1 | <0.1 |
| (d) | Oil | COCOS NUCIFERA (COCONUT) OIL | 0.5 | 0.5 | 0.5 | 0.5 | 0.5 |
| (f) | Cationic polymer | POLYQUATERNIUM-7 and GUAR HYDROXYPROPYLTRIMONIUM CHLORIDE | 0.56 | 0.56 | 0.56 | 0.56 | 0.56 |
| (h) | Silicone | DIMETHICONE and AMODIMETHICONE | 0.5 | 0.5 | 0.5 | 0.5 | 0.5 |
| | Fragrance | FRAGRANCE | | | | | |
| | Salt | SODIUM CHLORIDE | 0.93 | 0.93 | 0.93 | 0.93 | 0.93 |
| | Preservative | PHENOXYETHANOL, SALICYLIC ACID, and SODIUM BENZOATE | 0.7 | 0.7 | 0.7 | 0.7 | 0.7 |
| | pH modifier | CITRIC ACID | 0.15 | 0.15 | 0.15 | 0.15 | 0.15 |
| | Miscellaneous | FUMARIC ACID, SORBIC ACID, and ACETIC ACID | <0.1 | <0.1 | <0.1 | <0.1 | <0.1 |
| (e) | Water | WATER | 78.4 | 78.4 | 78.4 | 78.4 | 78.4 |

Example 6

Exemplary Composition B was evaluated in comparison to four comparative compositions (Comparative Compositions A-D). The foaming attributes of Exemplary Composition B and Comparative Compositions A-D were evaluated using a DFA100 Dynamic Foam Analyzer, which is commercially available from KRUSS. To assess the foam attributes using the DFA100 Dynamic Foam Analyzer, samples were prepared from each of Exemplary Composition B and Comparative Compositions A-D. Each sample contained 5 wt. % of the respective compositions and 95 wt. % of deionized water, based on the total weight of the sample. The samples were dispersed into a cylinder and mixed using a vertical blade stirrer to generate foam for 15 seconds. The total foam height was then measured at time=20 seconds.

In addition, Exemplary Composition B and Comparative Compositions A-D were uniformly applied to hair swatches and evaluated for wet smoothness and dry smoothness by an expert evaluator.

Table 3, provided below, shows the results for the foaming attributes, wet smoothness, and dry smoothness associated with Exemplary Composition B and Comparative Compositions A-D.

TABLE 3

| Attributes | Ex. B | Comp. A | Comp. B | Comp. C | Comp. D |
|---|---|---|---|---|---|
| Abundance | 96.3 | 102.5 | 97.3 | 84 | 86.4 |
| Foam Stability | great | good | good | bad | bad |
| Smoothness in Foam | ✓✓ | | | ✓ | ✓✓ |
| Smoothness in rinse | ✓✓ | | | ✓✓ | ✓ |
| Wet smoothness | ✓✓ | | ✓ | ✓ | ✓ |
| Dry smoothness | ✓✓ | | | | ✓ |

Exemplary Composition B exhibited surprising improvements to the foam stability as compared to Comparative Compositions A-D. The improvement in foam stability of Exemplary Composition B in comparison to Comparative Compositions A-D is unexpected because one of ordinary skill would expect the addition of a fatty alcohol in combination with a glucamide (Comparative Example C) or a fatty alcohol in combination with an alkanolamide (Comparative Example D) to provide "bad" foam stability or at least reduce the foaming properties of the composition based on the results of Comparative Examples C and D from Table 3. Comparative Composition B, which included a glucamide and an alkanolamide without a fatty alcohol, exhibited "good" foam stability. Thus, one of ordinary skill, if having knowledge of Table 3, would expect that the use of a glucamide, an alkanolamide, and a fatty alcohol would produce a foam stability that is between "good" and "bad." Further, one of ordinary skill would expect based on Comparative Examples C and D that Comparative Example B, which excludes fatty alcohol, would result in the best foam stability. However, Exemplary Composition B exhibited "great" foam stability and was superior to the foam stability of Comparative Example B. Thus, it is would be unexpected that Exemplary Composition B would exhibit superior foam stability as compared to Comparative Compositions A-D.

In addition, Exemplary Composition B unexpectedly provided simultaneous improvements in foam stability, smoothness in foam, smoothness in rise, wet smoothness, and dry smoothness. Notably, none of Comparative Compositions A-D provided "noticeably better" dry smoothness. Comparative Composition D was the only comparative composition that provided "better" dry smoothness. Thus, the unique combination of nonionic surfactants used in Exemplary Composition B provided an unexpected improvement in the dry smoothness as the dry smoothness valuation of Exemplary Composition B was better than the expected addition of the dry smoothness valuations of Comparative Compositions A-D.

The term "INCI" is an abbreviation of International Nomenclature of Cosmetic Ingredients, which is a system of names provided by the International Nomenclature Committee of the Personal Care Products Council to describe personal care ingredients.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

All components and elements positively set forth in this disclosure can be negatively excluded from the claims. In other words, the hair cleansing compositions of the instant disclosure can be free or essentially free of all components and elements positively recited throughout the instant disclosure.

In some instances, the hair cleansing compositions of the present disclosure may be substantially free of non-incidental amounts of the ingredient(s) or compound(s) described herein. A non-incidental amount of an ingredient or compound is the amount of that ingredient or compound that is added into the hair cleansing composition by itself. For example, a hair cleansing composition may be substantially free of a non-incidental amount of an ingredient or compound, although such ingredient(s) or compound(s) may be present as part of a raw material that is included as a blend of two or more compounds.

Some of the various categories of components identified may overlap. In such cases where overlap may exist and the hair cleansing composition includes both components (or the composition includes more than two components that overlap), an overlapping compound does not represent more than one component. For example, lanolin may be characterized as both an oil and a fatty compound. If a particular hair cleansing composition includes both an fatty compounds and an oil, lanolin will serve only as the fatty compound or only as the silicone (lanolin does not serve as both the fatty compound and oil).

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

As used herein, the terms "comprising," "having," and "including" are used in their open, non-limiting sense.

The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

The expression "one or more" means "at least one" and thus includes individual components as well as mixtures/combinations.

Other than in the operating examples, or where otherwise indicated, all numbers expressing quantities of ingredients and/or reaction conditions may be modified in all instances by the term "about," meaning within +/−5% of the indicated number.

The term "treat" (and its grammatical variations) as used herein refers to the application of the compositions of the present disclosure onto the surface of keratinous substrates such as hair on a user's head and/or body.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material. All of the components set forth herein may be optionally included or excluded from the compositions/method/kits. When excluded, the compositions/methods/kits may be free or essentially free of the component. For example, a particular composition may be free or essentially free of silicones.

What is claimed is:

1. A hair cleansing composition comprising:
   (a) about 8 to about 20 wt. % of a sulfate based anionic surfactant;
   (b) about 1 to about 2 wt. % of an amphoteric surfactant;
   (c) about 4 to about 10 wt. % of a plurality of nonionic surfactants, the plurality of nonionic surfactants comprising:
      (i) about 1 to about 1.5 wt. % of a fatty alcohol,
      (ii) about 1.5 to about 3 wt. % of a glucamide, and
      (iii) about 1.5 to about 5.5 wt. % of an alkanolamide that is not a glucamide,
         wherein a weight ratio of an amount of the fatty alcohols of (i) to an amount of the glucamide of (ii) is 1:1.5 to 1:2.5
   (d) about 0.5 to 1.5 wt. % of (g) coconut oil,
   (e) water;
   (f) about 0.01 to about 3 wt. % of a cationic polymer; and
   (h) about 0.1 to about 5 wt. % of a silicone,
      wherein all weight percentages are based on the total weight of the hair cleansing composition.

2. The hair cleansing composition of claim 1, wherein the sulfate based anionic surfactant is selected from sodium lauryl ether sulfate, sodium lauryl sulfate, ammonium lauryl ether sulfate, ammonium lauryl sulfate, and a mixture thereof.

3. The hair cleansing composition of claim 1, wherein the amphoteric surfactant is selected from lauryl betaine, lauroamphoglycinate, lauroamphopropylsulfonate, lauroamphopropionate, lauroampho-carboxyglycinate, lauryl sultane, myristamidopropyl betaine, myristyl betaine, myristoamphoglycinate, myristyl propionate, stearoamphoglycinate, stearoamphopropionate, stearoamphopropylsulfonate, stearyl betaine, cocamidoethyl betaine, cocamidopropyl betaine, cocamidopropyl hydroxysultaine, cocamidopropyl dimethylamine propionate, cocoamphoglycinate, cocoamphocarboxypropionate, cocoamphocarboxyglycinate, coco-betaine, cocoamphopropionate, cocoamphopropylsulfonate, and a mixture thereof.

4. The hair cleansing composition of claim 1, wherein the fatty alcohol is selected from cetearyl alcohol, cetyl alcohol, stearyl alcohol, behenyl alcohol, arachidyl alcohol, eicosyl alcohol, myristyl alcohol, 2-dodecylhexadecanol, 2-tetradecyl-1-octadecanol, 2-tetradecyl-1-eicosanol, 2-hexadecyl-1-octadecanol, 2-hexadecyl-1-eicosanol, and a mixture thereof.

5. The hair cleansing composition of claim 1, wherein the glucamide is selected from lauroyl/myristoyl methyl glucamide, capryloyl/capryl methyl glucamide, lauroyl methyl glucamide, myristoyl methyl glucamide, capryloyl methyl glucamide, capryl methyl glucamide, cocoyl methyl glucamide, capryloyl/caproyl methyl glucamide, cocoyl methyl glucamide, lauryl methylglucamide, oleoyl methylglucamide oleate, stearoyl methylglucamide stearate, sunfloweroyl methylglucamide, tocopheryl succinate methylglucamide, and a mixture thereof.

6. The hair cleansing composition of claim 1, wherein the alkanolamide has a carbon chain containing 2 to 36 carbons.

7. The hair cleansing composition of claim 6, wherein the alkanolamide comprises at least one of a fatty acid diethanolamide, fatty acid monoethanolamides, fatty acid monoisopropanolamides, fatty acid diisopropanolamides, or fatty acid glucamides.

8. The hair cleansing composition of claim 1, wherein the alkanolamide is selected from oleic acid diethanolamide, myristic acid monoethanolamide, soya fatty acids diethanolamide, stearic acid ethanolamide, oleic acid monoisopropanolamide, linoleic acid diethanolamide, stearic acid monoethanolamide, behenic acid monoethanolamide, isostearic acid monoisopropanolamide, erucic acid diethanolamide, ricinoleic acid monoethanolamide, coconut fatty acid monoisopropanolamide, coconut acid monoethanolamide, palm kernel fatty acid diethanolamide, coconut fatty acid diethanolamide, lauric diethanolamide, polyoxyethylene coconut fatty acid monoethanolamide, coconut fatty acid monoethanolamide, lauric monoethanolamide, lauric acid monoisopropanolamide, myristic acid monoisopropanolamide, coconut fatty acid diisopropanolamide, and a mixture thereof.

9. A method of cleaning hair comprising:
   (a) applying the hair cleansing composition of claim 1 to hair; and
   (b) rinsing the hair for removing the hair cleansing composition.

10. A method for preparing the hair cleansing composition of claim 1 comprising:
   (I) preparing a mixture comprising:
      (a) about 8 to about 20 wt. % of a sulfate based anionic surfactant;
      (b) about 1 to about 2 wt. % of an amphoteric surfactant;
      (c) about 4 to about 10 wt. % of a plurality of nonionic surfactants, the plurality of nonionic surfactants comprising:
         (i) about 1 to about 1.5 wt. % of a fatty alcohol,
         (ii) about 1.5 to about 3 wt. % of a glucamide, and
         (iii) about 1.5 to about 5.5 wt. % of an alkanolamide that is not the glucamide,
      (e) water,
      (f) about 0.01 to about 3 wt. % of a cationic polymer; and
      (h) about 0.1 to about 5 wt. % of a silicone,
   (II) applying heat to the mixture; and
   (III) adding (d) about 0.5 wt. % to 1.5 wt. % of coconut oil before or after applying heat to the mixture, wherein all weight percentages are based on the total weight of the prepared hair cleansing composition.

* * * * *